US008821591B2

(12) United States Patent
Iizaki et al.

(10) Patent No.: US 8,821,591 B2
(45) Date of Patent: Sep. 2, 2014

(54) HAIR DECORATION ARTICLE AND HAIR DYEING AND BLEACHING METHOD USING SAME

(75) Inventors: Takeshi Iizaki, Kawaguchi (JP); Naohiro Ando, Chiba (JP); Yoshimasa Takagi, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/114,339

(22) PCT Filed: Apr. 26, 2012

(86) PCT No.: PCT/JP2012/061228
§ 371 (c)(1),
(2), (4) Date: Nov. 29, 2013

(87) PCT Pub. No.: WO2012/147858
PCT Pub. Date: Nov. 1, 2012

(65) Prior Publication Data
US 2014/0130823 A1  May 15, 2014

(30) Foreign Application Priority Data

Apr. 28, 2011 (JP) ................... 2011-101533
Dec. 14, 2011 (JP) ................... 2011-273009

(51) Int. Cl.
*A61Q 5/10* (2006.01)
*A45D 19/02* (2006.01)

(52) U.S. Cl.
CPC .................. *A45D 19/02* (2013.01)
USPC ............ 8/405; 8/492; 8/636; 8/101; 132/202; 132/208

(58) Field of Classification Search
USPC ............... 8/405, 492, 636, 101; 132/202, 208
See application file for complete search history.

(56) References Cited

U.S. PATENT DOCUMENTS 6,332,726 B2   12/2001   Yamamoto et al.
2013/0174860 A1   7/2013   Takagi

FOREIGN PATENT DOCUMENTS

| JP | 10 290712 | 11/1998 | |
|---|---|---|---|
| JP | 2000 16470 | 1/2000 | |
| JP | 2006 169203 | 6/2006 | |
| JP | 2007 126415 | 5/2007 | |
| JP | 2007126415 | * 5/2007 | ............ A61Q 5/10 |
| JP | 2007 300958 | 11/2007 | |
| JP | 2012 16588 | 1/2012 | |

OTHER PUBLICATIONS

International Search Report Issued Jul. 31, 2012 in PCT/JP12/061228 Filed Apr. 26, 2012.

* cited by examiner

*Primary Examiner* — Eisa Elhilo
(74) *Attorney, Agent, or Firm* — Oblon, Spivak, McClelland, Maier & Neustadt, L.L.P.

(57) ABSTRACT

A hair cosmetic article includes a composition A including an alkali agent; a composition B including an oxidizing agent; a composition C including a powdery oxidation assistant; and a hair cosmetic applicator including a container part (4) in which a hair cosmetic material (3) produced by mixing the compositions A, B and C and having a viscosity of 3 to 30 Pa·s at 30° C., an application part (2) by which the hair cosmetic material (3) is applied to a hair-bundle, and an extension part (5) having a liquid-leading passage (51) which communicates the container part (4) to the application part (2). The application part (2) includes a discharge port (21) and a comb part (23), and the comb part (23) includes a plurality of comb teeth (22) which are disposed substantially annularly so as to surround the discharge port (21).

24 Claims, 3 Drawing Sheets

HAIR DECORATION ARTICLE AND HAIR DYEING AND BLEACHING METHOD USING SAME

CROSS REFERENCE TO RELATED APPLICATION

This application is a 371 of PCT/JP2012/061228, filed on Apr. 26, 2012, and claims priority to the following Japanese Patent Applications: 2011-101533, filed on Apr. 28, 2011; and 2011-273009, filed on Dec. 14, 2011.

TECHNICAL FIELD

The present invention relates to a hair cosmetic article and a hair dyeing and bleaching method using the same.

BACKGROUND ART

According to a conventional hair dyeing or bleaching treatment, an operation in which a hair cosmetic material put on a bottom of a shallow-bottomed vessel is sent onto an applying tool and the material is applied to the hair is repeated. The repeated operation often causes the failure of the treatment, because such an operation is complicated. In order to eliminate this repeated operation, an integrated storage part-application part hair dyeing tool is proposed in which a hair cosmetic material is supplied to an application part from the storage part of the hair cosmetic material through a connection part (see, for example, Patent Literature 1). A hair dyeing or bleaching treatment using such a storage part application part integrated hair dyeing tool, however, has a new problem in which discharging property of a hair cosmetic material is worsen.

Apart from this technique, in order to obtain clear treatment effects in the hair dyeing or bleaching, high decoloring power is necessary. To that end, a hair cosmetic material using a powdery oxidation assistant such as persulfate is proposed (see, for example, Patent Literature 2). When the powdery oxidation assistant is used for obtaining the clear effects of the treatment, and at the same time the integrated hair dyeing tool is used for simplifying the applying operation, however, a new problem arises in which it is difficult to prepare a hair cosmetic material by mixing and dispersing the powdery oxidation assistant with and in other components in the storage part of the integrated hair dyeing tool. In addition, a new problem in which the discharging property of the hair cosmetic material is worsen also arises. When the viscosity of the hair cosmetic material is reduced to increase the fluidity thereof in order to solve these problems, the hair cosmetic material easily drips when it is applied to the hair. In addition, after it is applied, the hair cosmetic material easily adheres to parts other that the desired part of the hair or parts other than the hair.

Incidentally, the hair dyeing and bleaching is divided into whole dyeing in which all the hair is uniformly dyed, and partial dyeing, which is also called highlighting or lowlighting, in which a part of the hair is selected and the part is dyed. In the case of the whole dyeing, the dyeing operation is comparatively easy because it is not necessary to select a specific part. On the other hand, the operation of the partial dyeing is comparatively complicated. The part of the hair to be dyed is pulled out in layers from the head using a tapered tail part of a comb which is called a tail comb, and a dyeing agent is applied to the hair with a brush. It is difficult, however to perform such an operation that is performed in a hair salon, for a person by oneself.

A special tool for performing the partial dyeing by oneself, therefore, has been proposed. For example, Patent Literature 3 proposes a nozzle for hair dyeing in which a pair of opening channels is disposed at a tip of a hollow cylindrical nozzle body in which a flowing route for letting a coloring agent flow is formed. A space between the pair of the opening channels is made to be able to insert the hair to be dyed. When the partial dyeing is performed, the hair bundle which is intended to be dyed is inserted into the opening channels of the nozzle attached to a discharging vessel. After that, the tip of the nozzle is positioned at a base part of the part, and the nozzle is moved from the base part of the hair to be dyed to the hair ends while the discharging vessel is pressed. As the hair dyeing agent is discharged in the opening channels, thus the desired part of the hair can be dyed.

When the nozzle described in Patent Literature 3 is used, however, it is difficult to completely dye the base part of the hair to be dyed. This is because it is difficult to completely approach the opening channels to the base part of the hair in a given width of a base end of the nozzle (a connecting part to the vessel). In addition, when using the nozzle described in the same literature, it is necessary that the hair is inserted into the space between the pair of the opening channels in the state in which the hair is set up by taking the hair ends with fingers, and thus the hair most ends cannot be also dyed.

CITATION LIST

Patent Literature

Patent Literature 1: US2001/0040173A1
Patent Literature 2: JP2006-169203A
Patent Literature 3: JP10-290712A

SUMMARY OF INVENTION

The present invention provides A hair cosmetic article including:
   a composition A including an alkali agent;
   a composition B including an oxidizing agent;
   a composition C including a powdery oxidation assistant; and
   a hair cosmetic applicator including a container part in which a hair cosmetic material produced by mixing the compositions A, B and C and having a viscosity of 3 to 30 Pa·s at 30° C. is to be contained; an application part by which the hair cosmetic material is applied to a hair-bundle; and an extension part having a liquid-leading passage which communicates the container part to the application part,
wherein
   the application part includes a discharge port and a comb part, and the comb part includes a plurality of comb teeth which are disposed substantially annularly so as to surround the discharge port.

The present invention also provides a hair cosmetic article including:
   a composition A including an alkali agent;
   a composition B including an oxidizing agent;
   a composition C including a powdery oxidation assistant; and
   a hair cosmetic applicator including a container part in which a hair cosmetic material produced by mixing the compositions A, B and C and having a viscosity of 3 to 30 Pa·s at 30° C. is to be contained; an application part by which the hair cosmetic material is applied to a hair-bundle; and an extension part having a liquid-leading passage which communicates the container part to the application part, wherein the hair cosmetic material has a pH of 8.0 to 12.5 at 25° C., a value of a/b is from 0.1 to 5 wherein a denotes a diameter (mm) of the narrowest part of the liquid-leading passage and b denotes a viscosity (Pa·s) of the hair cosmetic material at 30° C., a value of c/b is from 0.5 to 15 wherein c denotes a percentage (%) of a volume of a head space to a volume of the container part in the state in which the hair cosmetic material is contained in the container part, and the hair cosmetic applicator has a whole length of 5 to 40 cm.

The present invention further provides a hair dyeing or bleaching method using a hair cosmetic article, the hair cosmetic article including:

a composition A including an alkali agent;

a composition B including an oxidizing agent;

a composition C including a powdery oxidation assistant; and a hair cosmetic applicator including a container part in which a hair cosmetic material produced by mixing the compositions A, B and C and having a viscosity of 3 to 30 Pa·s at 30° C. is to be contained; an application part by which the hair cosmetic material is applied to a hair-bundle; and an extension part having a liquid-leading passage which communicates the container part to the application part, wherein the application part includes a discharge port and a comb part, and the comb part includes a plurality of comb teeth which are disposed substantially annularly so as to surround the discharge port, the method including the steps 1) to 3) of:

1) a step of mixing the compositions A, B and C in the container part to produce the hair cosmetic material in the container part;

2) a step of supplying the hair cosmetic material to the application part from the container part through the liquid-leading passage in the extension part using the hair cosmetic applicator, the hair cosmetic applicator being in the state in which the container part in which the hair cosmetic material is contained, the application part, and the extension part are assembled; and 3) a step of applying the hair cosmetic material supplied to the application part to hair.

Advantageous Effects of Invention

The present invention provides a hair cosmetic article, which provides a good mixability when each composition is mixed in the container part of the applicator, and a hair cosmetic material, produced by mixing the composition, having an appropriate fluidity. The hair cosmetic article of the present invention shows prominent effects particularly in partial hair dyeing, especially in application in stripes.

DESCRIPTION OF EMBODIMENTS

Figure 1:
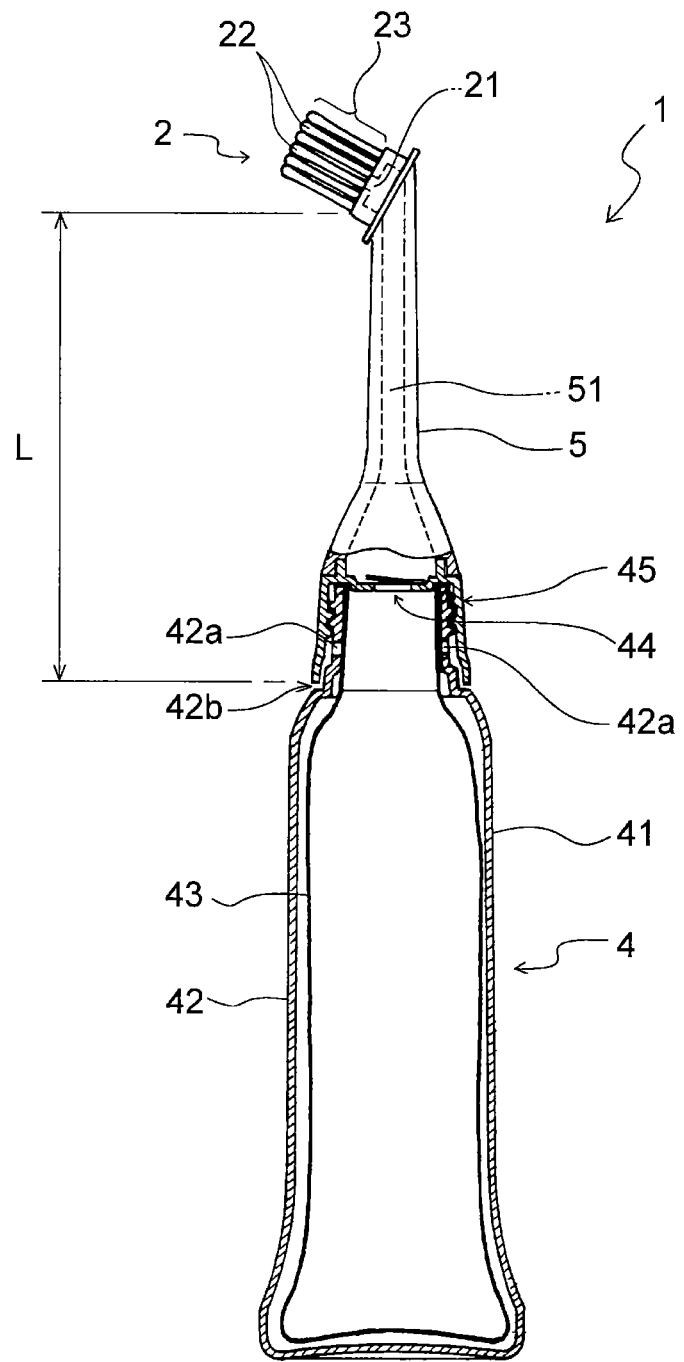
FIG. 1 is a partially cutaway side view showing one embodiment of a hair cosmetic applicator used in a hair cosmetic article of the present invention.

The present invention will be explained based on preferable embodiments below. A hair cosmetic article of the present invention is mainly applied to hair, and is used for hair dyeing, bleaching or dye removal. In the present invention, when the hair cosmetic article includes a dye, the hair cosmetic article is used for dyeing hair, and when it does not include a dye, it used for bleaching hair. In addition, when the hair cosmetic article of the present invention is used for hair to which a hair dye has been applied, the hair cosmetic article is used for destaining the hair. The hair cosmetic article includes at least four elements of (i) a composition A including an alkali agent, (ii) a composition B including an oxidizing agent, (iii) a composition C including a powdery oxidation assistant, and (iv) a hair cosmetic applicator, and is in a kit in which these elements are contained in one package. Alternatively, the hair cosmetic article includes at least three elements of (i') a composition A' including an alkali agent and a powdery oxidation assistant, (ii) a composition B including an oxidizing agent, and (iv) a hair cosmetic applicator, and is in the state of a kit in which these elements are contained in one package. In addition, the hair cosmetic article includes at least three elements of (i") a composition A" including an alkali agent and a surfactant, (ii) a composition B including an oxidizing agent, and (iv) a hair cosmetic applicator, and is in the state of a kit in which these three elements are contained in one package. In any hair cosmetic kit, the composition A, the composition B, the composition C, the composition A' and the composition A" are each independently contained in separate containers. Each composition is sealed in the container, before the use of the hair cosmetic article of the present invention.

When the hair cosmetic article of the invention is a hair dyeing cosmetic, the composition A includes a dye in addition to the alkali agent, the composition A' includes a dye in addition to the alkali agent and the powdery oxidation assistant, and the composition A" includes a dye in addition of the alkali agent and the surfactant. When the hair cosmetic article of the invention is a cosmetic for bleaching, the composition A does not include a dye but includes the alkali agent, the composition A' does not include a dye but includes the alkali agent and the powdery oxidation assistant, and the composition A" does not include a dye but includes the alkali agent and the surfactant. Regardless of whether the hair cosmetic article of the invention is for hair dyeing or bleaching, the composition A may be in the state of liquid, cream, paste, or powder, preferably in the state of liquid or cream, more preferably in the state of liquid. The composition A' may be in the state of liquid, cream, paste, or powder, preferably in the state of a powder or paste, more preferably in the state of a powder. The composition A" may be in the state of liquid, cream, paste, or powder, preferably in the state of liquid or cream.

The composition B may be in the state of liquid, cream or paste, regardless of whether the hair cosmetic article of the invention is for hair dyeing or bleaching, preferably in the state of liquid or cream, more preferably in the state of liquid. The composition C is generally in the state of a powder.

As state above, each composition is independently sealed in a separate container.

When the composition is liquid, as a container for housing the composition, for example, a bottle having a neck part opening upward, the neck part being able to be closed with a closing member, may be used. When the composition is a cream, as a container for housing the composition, for example, a tube may be used. When the composition is a powder, a container for housing the composition, for example, a pouch may be used.

FIG. 1 is a partially cutaway side view showing one embodiment of a hair cosmetic applicator (hereinafter may be referred to as an "applicator"), which is one element of the hair cosmetic article of the present invention. The applicator 1, as shown in FIG. 1, has an application part 2 having an agent discharge port 21 and a comb part 23 which formed of multiple comb teeth 22 disposed substantially annularly so as to surround the agent discharge port 21; and a container part 4 which contains a hair cosmetic material (not shown) and is capable of supplying the hair cosmetic material to the application part 2. The applicator 1 also has an extension part 5 having a liquid-leading passage 51 to supply the hair cosmetic material to the application part 2 from the container part 4.

Figure 2:
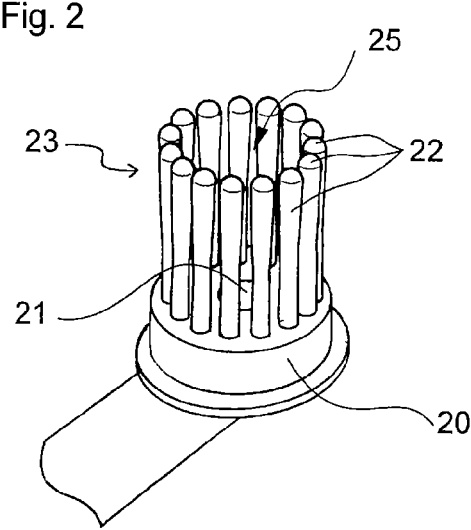
FIG. 2 is an enlarged perspective view of an application part in the hair cosmetic applicator shown in FIG. 1.
Figure 3:
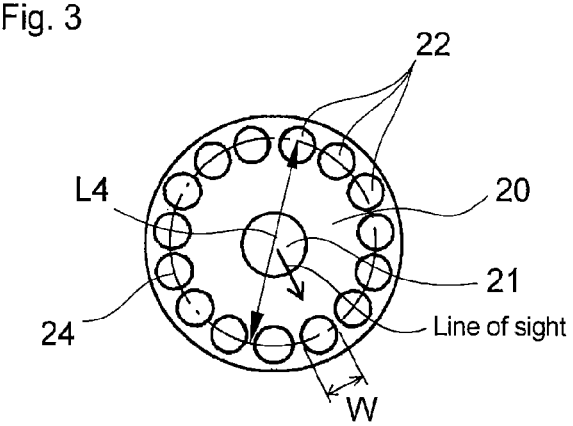
FIG. 3 is a plan view of a comb teeth stand in the application part in the hair cosmetic applicator shown in FIG. 1, which is seen from a side at which the comb part protrudes.

The application part 2 is a part bringing into contact with hair, and is formed so that the hair cosmetic material can be applied to the hair while combing the hair with the comb part 23. The application part 2 has, as shown in FIG. 2 and FIG. 3, a circular comb teeth stand 20 in a planer view, and the agent discharge port 21, from which the hair cosmetic material supplied through the extension part 5 is discharged, opens at a central part of the comb teeth stand 20. A number of the comb teeth 22 are substantially annularly stood on the comb teeth stand 20 so as to surround the agent discharge port 21. The cylindrical comb part 23 is formed on the comb teeth stand 20 by the comb teeth 22. The comb teeth 22 and the comb teeth stand 20 are integrally molded from a synthetic resin. The comb teeth 22 have, as shown in FIG. 3, a circular plane shape and a circular cross-sectional shape, and they are disposed at even intervals on a circular line 24 surrounding the agent discharge port 21. It is not necessary, however, that they are disposed on the circular line 24, so long as the comb teeth 22 are disposed so that a track obtained by disposing them draws an isotropic figure. For example, it is enough that respective comb teeth 22 are disposed so that a regular polygon such as a regular triangle, regular hexagon or regular octagon is drawn. The term "substantially annularly" in the present invention has a concept including such a regular polygon.

Figure 4:
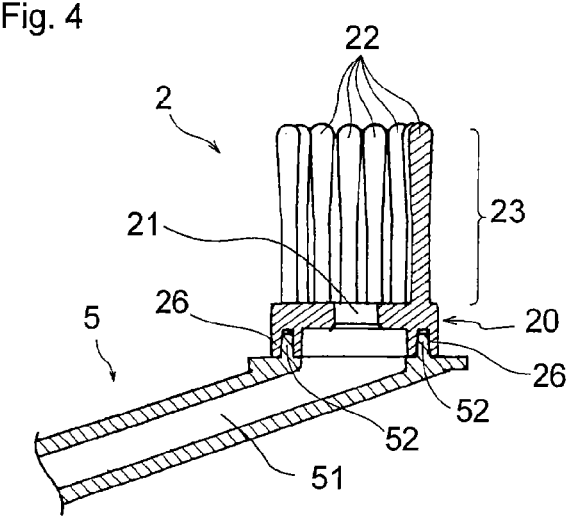
FIG. 4 is a partially sectional view showing a connection state between the application part and an extension part in the hair cosmetic applicator shown in FIG. 1.

As shown in FIG. 4, an upper end of the extension part 5 opens, and an annular rib 52 is protruded at an opening edge. On the other hand, an annular groove 26, which has a shape complementary with the annular rib 52, is recessed on an underside of the comb teeth stand 20 in the application part 2. The extension part 5 is combined with the application part 2 by fitting the annular rib 52 and the annular groove 26. A lower end of the extension part 5 is capable of fitting to an upper end of a connection cap 45 described below (see FIG. 1), and the extension part 5 is combined with the connection cap 45 by such a fitting.

Returning back to FIG. 1, the container part 4 is formed of a double nested container including a container body 41 having a squeezable bottomed cylindrical outer container 42, and an inner bag 43, which is disposed in the outer container 42 and whose port is air-tightly joined to an inside surface of a cylindrical port of the outer container 42; and a connection cap 45 with a check valve 44 attached to a neck part of the container body 41. A screw thread is provided on an inside surface of the connection cap 45, and this screw thread is capable of screwing with a screw thread provided on an outer surface of the neck part of the container body 41. When the outer container 42 of the container part 4 is clasped with one hand and the outer container 42 is squeezed with the hand, the outer container 42 itself or air between the outer container 42 and the inner bag 43, presses the inner bag 43 inside, whereby the hair cosmetic material in the inner bag 43 is pushed and is supplied to the agent discharge port 21 through the liquid-leading passage 51. An upper part of the connection cap 45 is combined to the extension part 5 for forming a given interval between the container part 4 and the application part 2, and the other end of the extension part 5 is combined to a back surface side of the comb teeth stand 20. The extension part 5 has a liquid-leading passage 51 in its inside, and the container part 4 is communicated with the agent discharge port 21 through the liquid-leading passage 51.

A suction port 42a is formed at a cylindrical port of the outer container 42 for communicating a space between the outer container 42 and the inner bag 43 with the outside of the outer container 42. When the outer container 42 deformed by pressing force is restored to its original state by an elastic restoring force, air outside of the container 1 is flown into a space between the outer container 42 and the inner bag 43 passing through a space 42b formed between the lower end of the connection cap 45 and the outer container 42, and the suction port 42a. When the container part 4 is made so as to have such a structure, the hair cosmetic material, which is the content, can be gradually discharged from the agent discharge port 21 by repeating the deformation operation by pressing the circumference surface.

When such a double nested container is used for the container part 4, even if a residual quantity of the hair cosmetic material inside is reduced, it can be prevented to deflate the container part 4 whereby it is difficult to clasp the container part. In addition, a check valve 44 is formed in the connection cap 45, the liquid-leading passage 51, which communicates the space in the container part 4 with the agent discharge port 21, or the like to prevent a reverse flow of air into the liquid-leading passage 51 or container part 4 after the discharge of the agent, thereby preventing the difficulty in discharge of the hair cosmetic material and scattering of the hair cosmetic material, when the agent is discharged at next time. Furthermore, when the check valve 44 is provided, even if the application part 2 and the container part 4 are disposed in any spatial positional relation, the hair cosmetic material can be supplied to the application part 2. A distance L from a part of outer container 42 in the container part 4 which is not covered with the connection cap 45 to the comb part 23 (see FIG. 1) is preferably from 40 to 200 mm, more preferably from 70 to 120 mm, even more preferably from 80 to 100 mm, in the terms of the improved visual confirmation of the state of hair to which it is applied, and easiness of applying operation.

The applicator 1 having such a structure is in a disassembled state before the hair cosmetic article of the present invention is used. It is, for example, in a two-part state of the container body 41, and a combined component of the three of the application part 2, the extension part 5 and the connection cap 45.

When the hair cosmetic article of the present invention is used, the compositions are mixed to produce a hair cosmetic material. The mixing is attained by, for example, putting the compositions A, B and C in the container, putting the compositions A and B in the container, followed by putting the composition C, putting the compositions A and C in the container, followed by putting the composition B, or putting the compositions B and C, followed by putting the composition A. More specifically, the mixing is attained by putting the compositions A and C in the container in which the composition B is contained, putting the composition A in the container in which the composition B is contained, and then putting the composition C therein, or putting the composition C in the container in which the composition B is contained, and then putting the composition A therein. Of these, it is preferable to put the composition C in the container in which composition B is contained, and then put the composition A therein, for the mixing is performed successfully. If the composition B is mixed with the composition C A before the composition B is mixed with the composition, the obtained mixture easily has an increased viscosity, and thus the mixing with the composition C, which is subsequently added, may be unsuccessfully performed.

When the compositions A' and B are used, the mixing can be attained by, for example, putting the compositions A' and B in the container. More specifically, it is preferable to put the composition A' in the container in which the composition B is contained.

When the compositions A" and B are used, the mixing can be attained by, for example, putting the compositions A" and B in the container. More specifically, the mixing can be attained by putting the composition A" in the container in which the composition B is contained. Alternatively, the mixing can also be attained by putting the composition B in the container in which the composition A" is contained. Of these, it is preferable to put the composition A" in the container in which the composition B is contained, for successfully performing the mixing.

Instead of these mixing modes, the mixing can also be performed by putting each composition in a blank container, which has been added to a package of kit, in the order described above. In any case, it is advantageous to use the container part 4, which is a part of the applicator 1 described above, as the container used for mixing the each composition. In this case, an advantage in which the number of the containers contained in the kit can be decreased when the container part 4 is used as a container for containing the composition B before the hair cosmetic article is used, and the container part 4 is used as a container for containing the hair cosmetic material during the use of the hair cosmetic article.

When the compositions are put in the container part 4, the opening of the container part 4 is closed with the closing member, and the container is shaken in the closed state to promote the mixing of the each composition, thereby producing the hair cosmetic material. Alternatively, the opening of the container part 4 may be closed the extension part 5 to which the application part 2 is attached, and the container is shaken in such a closed state, whereby the mixing of the each composition can be promoted.

Specifically, (a) the container part 4 in which the compositions A, B and C are contained may be shaken to promote the mixing of the each composition. Also, (b) the container part 4 in which the compositions B and C are contained may be shaken, and then the composition A is put in the container part 4 and the obtained container part 4 may be shaken again to promote the mixing of the each composition. In addition, (c) the container part 4 in which the compositions A and the C are contained may be shaken, and then the composition B is put in the container part 4 and the obtained container part 4 may be shaken again to promote the mixing. Further, (d) the container part 4 in which the compositions A and B are contained may be shaken, and then the composition C is put in the container part 4 and the obtained container part 4 may be shaken again to promote the mixing. Of these, (b) is preferable because the mixing was successfully performed.

When the mixing of the each composition is completed to produce the hair cosmetic material, the material is applied to hair. When the opening of the container part 4 is closed with the closing member, the closing member is taken out from the opening, and then the extension part 5 to which the application part 2 is attached may be attached to the container part 4, whereby the hair cosmetic applicator 1 is completed in a state in which the container part 4 in which the hair cosmetic material is contained, the application part 2, and the extension part 5 are assembled. In a case where the closure was performed by attaching the extension part 5 to which the application part 2 is attached to the opening of the container part 4 when the compositions are mixed, the hair cosmetic applicator 1 is completed in a state in which the container part 4 in which the hair cosmetic material is contained, the application part 2, and the extension part 5 are assembled at the time when the mixing is completed. Then, using this hair applicator 1, the hair cosmetic material is applied to the hair. The specific operations are performed as shown below.

Figure 5:
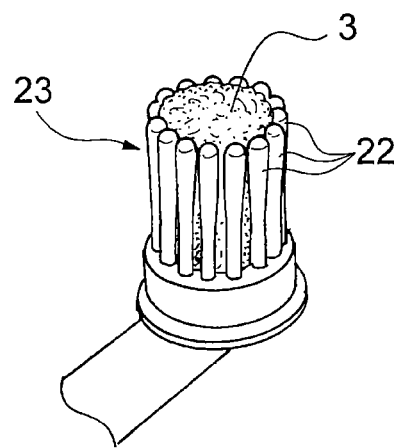
FIG. 5 is a perspective view showing a state in which a liquid or frothy hair cosmetic material is retained in a space inside the cylindrical comb part in the hair cosmetic applicator shown in FIG. 1.
Figure 6:
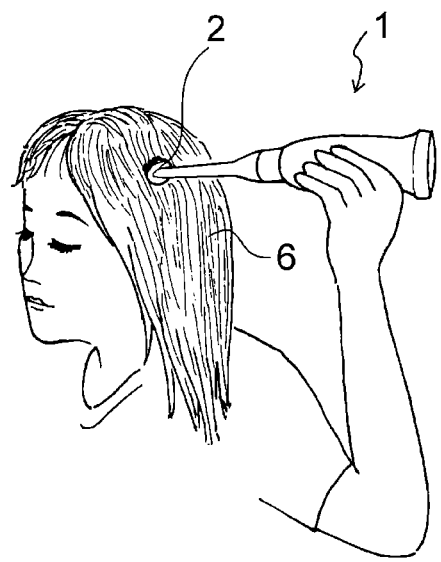
FIG. 6 is a perspective view showing a state in which a hair cosmetic material is applied to hair using the hair cosmetic applicator shown in FIG. 1.

First, the hair cosmetic material in the container part 4 is sent to the application part 2 by clasping the outer container 42 with one hand, and repeatedly squeezing it, and the hair cosmetic material is discharged from the agent discharge port 21. Then, as shown in FIG. 5, a desired amount of the hair cosmetic material 3 is stored inside of the cylindrical comb part 23. Next, the application part 2 in which the hair cosmetic material 3 is held is, as shown in FIG. 6, moved to the head, and the comb part 23 is pressed on the hair side. Subsequently, the application part 2 is moved in a direction of hair ends, and the hair treating agent 3 is applied to the hair inserted between the adjacent comb teeth 22 while the hair was combed with the comb part 23. As the comb teeth 22 in the agent discharge port 21 are disposed so that the track drawn by the comb teeth 22 is an substantially circle, which is an isotropic figure, as described above, even if the direction of the application part 2 is accidentally changed while the application part 2 is in motion, the application width of the hair cosmetic material is not substantially changed, and thus the hair cosmetic material can be easily applied in an substantially constant width.

The comb tooth 22 has a height of preferably from 5 to 30 mm, more preferably from 5 to 20 mm, even more preferably from 7 to 17 mm in a case of women with medium-length hair of about 20 to 25 cm, in order to be able to apply the agent in a given application width and length by one application operation in which the application part 2 is moved from the top of the head to the hair ends one time, and to prevent leakage of the cosmetic from the spaces between the comb teeth 22. From the same viewpoints, a circular line 24 which circumscribes a cross-section of a base end part of each of the comb teeth 22, and passes a center of the cross-section of the base end part of each of the comb teeth 22 has an internal diameter L4 of preferably from 5 to 30 mm, more preferably from 5 to 20 mm, even more preferably from 5 to 15 mm, further even more preferably from 8 to 13 mm. Such a range of the internal diameter L4 is also a range of preferable line width when highlighting or lowlighting is performed. When the internal diameter L4 is set within the range described above, the line width of the highlighting or lowlighting can be appropriately controlled, whereby a natural finish can be attained. In the present invention, the highlighting or lowlighting refers to a hair dyeing in which a part of the hair is dyed or bleached in a strip shape from the base to the hair ends. In the present invention, the internal diameter of the comb part refers to an internal diameter of a circular line which circumscribes a cross-section of a base end part of each of the comb teeth 22, and passes a center of the cross-section of the base end part of each of the comb teeth 22. The comb teeth 22 has a width W of preferably from 0.1 to 5 mm, more preferably from 0.1 to 3 mm, even more preferably from 0.5 to 2.5 mm, in order to increase the mechanical strength of the comb teeth and easily insert the comb teeth into the hair. The width W refers to a projection width when the comb teeth are seen from the central part side of the agent discharge port (FIG. 3).

In the hair cosmetic article of the present invention including the kit including the compositions and the applicator 1 as the constituent elements, as a result of the inventors' studies, it has been found that, in order to easily attain the clear operation effects, it is advantageous to keep three factors (a), (b) and (c), which affect to each other, in balance.

(a) A viscosity of the hair cosmetic material.
(b) A diameter and a length of the liquid-leading passage 51 in the extension part 5.
(c) A percentage of a volume of a head space in the container part 4 in the state in which the hair cosmetic material 3 is contained in the container part to the volume of the container part 4.

With respect to (a) described above, when the hair cosmetic material 3 produced by mixing the each composition has a low viscosity, the fluidity thereof is high, thus there is an advantage in which the composition C or composition A', including the powdery oxidation assistant, can be uniformly mixed and dispersed. In addition, there is an advantage in which the hair cosmetic material 3 has an excellent applying property and discharging property. When the composition A" and the composition B are used, advantageously, the composition A" and the composition B can be easily uniformly mixed and dispersed. On the other hand, however, there is a defect that the hair cosmetic material 3 easily drips when it is applied to the hair, to reduce usability. On the contrary, when the hair cosmetic material 3 has a high viscosity, there is an advantage in which it is difficult to drip the hair cosmetic material 3 on the application thereof, thus resulting in good usability. On the other hand, however, there is a defect in which it is not easy to uniformly mix and disperse the composition C or the composition A', including the powdery oxidation assistant, or in which the applying property and the discharging property of the hair cosmetic material are worsen. When the composition A" and the composition B are used, there is a defect in which it is not easy to uniformly mix and disperse the composition A" and the composition B. As described above, the improvement of the uniform dispersibility or mixability of the powdery oxidation assistant is inconsistent with the improvement of the applying property and the usability of the hair cosmetic material. When the composition A" and the composition B are used, the improvement of the uniform dispersibility and the mixability of the composition A" and the composition B is inconsistent with the improvement of the applying property and the usability of the hair cosmetic material.

With respect to (b) described above, when the diameter of the liquid-leading passage 51 in the extension part 5 is large, a space for smoothly moving the hair cosmetic material 3 from the container part 4 to the application part 2 is sufficiently secured, and thus there is an advantage in which the discharging property of the hair cosmetic material 3 becomes good. When the diameter of the liquid-leading passage 51 is large, however, if the extension part 5 has a too long length, there is a defect in which it is necessary to repeat the squeezing operation of the container part 4 multiple times for squeezing a sufficient amount of the hair cosmetic material 3. In addition, if the extension part 5 has a too long length or too short length, the operability of the applicator 1 is reduced.

With respect to (c), in the present invention, it is preferable to form a head space in the container part 4. The composition C and the composition A', used in the present invention, include the powdery component, and it is necessary to promote the mixing by shaking when the components are mixed, because it is difficult to mix the component with other components. In order to effectively perform the shaking, a sufficient head space is secured in container part 4, which is a container used for mixing the each composition, in the state where the compositions are contained in the part. When the percentage of the volume of the head space to the volume of the container part 4 is high, accordingly, there is an advantage in which a sufficient space where the compositions are moved is secured when the hair cosmetic material is produced by mixing the each composition to improve the mixability. On the other hand, however, there are also defects in which it is difficult to clasp the container part 4 because of the large volume of the container part 4, and eventually it is difficult to squeeze it, and in which it takes up a large area on a display space of commercial products because of the bulky package of the kit. On the contrary, when the percentage of the volume of the head space to the volume of the container part 4 is low, there is an advantage in which the package of the kit can be made smaller because the volume of the container part 4 can be decreased. On the other hand, however, there is a defect in which it is difficult to sufficiently mix the compositions. In addition, the volume of the head space is related to the viscosity of the hair cosmetic material 3, and when the hair cosmetic material 3 has a low viscosity, the mixing can be sufficiently performed even if the head space has a comparatively small volume. On the contrary, when the hair cosmetic material 3 has a high viscosity, it is necessary to secure a head space with a sufficient volume.

As described above, because the factors (a), (b) and (c) affect to each other, therefore, for example, when the hair cosmetic material 3 has a high viscosity and thus it is expected to decrease the discharging property or the mixability, advanced controls are required, for example, to increase the diameter of the liquid-leading passage 51, or to increase the percentage of the volume of the head space to the volume of the container part 4. In addition, as a result of the increased percentage of the volume of the head space to the volume of the container part 4, it is expected the whole length of the applicator 1 becomes long, an advance control to shorten the extension part 5 is required.

In accordance with the situations described above, the present inventors have various studied; as a result, it has been found that when a value of a/b, wherein a denotes a diameter (mm) of the narrowest part of the liquid-leading passage 51 and b denotes a viscosity (Pa·s) of the hair cosmetic material 3 at 30° C., is set at 0.1 to 5, preferably 0.2 to 4, more preferably 0.3 to 2, even more preferably 0.4 to 1, the discharging property of the hair cosmetic material 3 can be improved, and the discharge amount can be easily controlled. When the cross-section of the liquid-leading passage 51 is a circle, a diameter of the circle corresponds to the diameter a of the narrowest part described above. When the cross-section of the liquid-leading passage 51 is a shape other than the circle, a diameter of the corresponding circle obtained based on the cross-sectional area is presumed as the diameter a. The viscosity b of the hair cosmetic material 3 at 30° C. is a value obtained by measuring the hair cosmetic material at 30° C. for one minute under conditions of Spindle No. 4 and the number of revolution of 30 rpm using a B-type viscometer (B-type rotational viscometer (Model TV-10) manufactured by TOKYO KEIKI Inc.) Provided that when the viscosity is more than 2 Pa·s, b is a value obtained after the rotation at 30° C. for one minute under the conditions of spindle No. T-C and the number of revolution of 10 rpm using a B-type viscometer (B8R-type rotational viscometer (Model TVB-10) manufactured by TOKYO KEIKI Inc.). The measurement is performed immediately after the compositions A, B and C, and the temperature change due to the reaction heat is ignored.

When the hair cosmetic article of the present invention satisfies the relationship described above, the diameter a of the liquid-leading passage 51 itself is set at preferably 2 to 50 mm, more preferably 3 to 30 mm, even more preferably 3 to 15 mm, further even more preferably 5 to 10 mm. When the diameter a of the liquid-leading passage 51 is set within this range, not only the discharging property and the controllability of the discharged amount of the hair cosmetic material 3 can be improved, but also the retention during clasping the applicator 1 with the hand becomes good and the design of the applicator 1 can be improved. On the other hand, the viscosity of the hair cosmetic material 3 itself is set at 3 to 30 Pa·s at 30° C., preferably 5 to 15 Pa·s, more preferably 7 to 13 Pa·s, even more preferably 8.5 to 13 Pa·s. When the viscosity of the hair cosmetic material 3 is set within this range, not only the discharging property of the hair cosmetic material 3 can be improved, but also it can be effectively prevented the hair cosmetic material 3 from dripping during the application, and extendability of the hair cosmetic material 3 on the hair can also be improved. In particular, when the hair cosmetic material 3 used in the present invention includes the compositions A, B and C, or includes the compositions A' and B, the relationship of the a/b described above is peculiar to fluid in a specific state, because the hair cosmetic material 3 is special fluid which is liquid including the powdery component.

The hair cosmetic article of the present invention preferably satisfies a relationship described below, in addition to or in place of the relationships described above. A value of c/b wherein c (%) denotes a percentage (%) of a volume of a head space to a volume of the container part 4 in the state in which the hair cosmetic material 3 is contained in the container part 4, is preferably from 0.5 to 15, more preferably from 0.6 to 13, even more preferably 0.8 to 10, further even more preferably from 1 to 7. The value of c/b is a measure about how much the hair cosmetic material 3 can be easily shaken in the container part 4. When the value of c/b is within the range described above, the each composition (in particular the composition C including the powdery oxidation assistant) is certainly mixed, and thus the hair cosmetic material 3 having the desired viscosity can be obtained, and the occurrence of unevenly hair dyeing or bleaching can be prevented. When the hair cosmetic material 3 used in the present invention includes the compositions A, B and C, or includes the compositions A' and B, the relationship of c/b is also peculiar to fluid in a specific state in which the hair cosmetic material 3 includes the powdery component, as in the relationship of a/b described above.

In relation to the value of c/b, the volume percentage c of the head space is preferably from 5 to 90%, more preferably from 10 to 80%, even more preferably from 15 to 70%. The volume of the head space refers to a volume of a space in the container part 4 in a state immediately after putting the composition C in the container part 4 in which the composition B is contained, closing it, shaking the container part 4 to promote the mixing, subsequently putting the composition A in the container part 4, and shaking the obtained container part 4 again to promote the mixing, when the hair cosmetic material including the compositions A, B and C is used. The volume of the head space refers to a volume of a space in the container part 4 in a state immediately after the composition A' is put in the container part 4 in which the composition B is contained, the container is closed, and the obtained container part 4 is shaken again to promote the mixing, when the hair cosmetic material including the compositions A' and B is used. This volume of the head space refers to a volume of a space in the container part 4 in a state immediately after the composition A" is put in the container part 4 in which the composition B is contained, the container is closed, and the obtained container part 4 is shaken again to promote the mixing, when the hair cosmetic material including the compositions A" and B is used. The percentage of the volume of the head space is measured by the following procedure. (1) After the mixing of the compositions A, B and C, the compositions A' and B, or the compositions A" and B is promoted as described above, the height of the upper surface of the hair cosmetic material in the container part 4 is marked. (2) After this container part 4 is emptied, water is added up to the marked height, and a mass thereof is measured. The mass is converted into a volume. The volume is defined as E ($cm^3$). (3) The empty container part 4 is filled with water, and a mass thereof is measured. The mass is converted into a volume. The volumes is defined as F ($cm^3$). (4) A value calculated from the formula: $(1-E/F) \times 100$ is defined as a percentage of the volume of the head space wherein a density of water is 1 $g/cm^3$. In relation to the volume of the head space, the volume of the container part 4 itself is preferably from 3 to 300 $cm^3$, more preferably from 20 to 200 $cm^3$, even more preferably from 50 to 160 $cm^3$. When the volume of the container part 4 is set within this range, an amount of the hair cosmetic material 3 necessary and sufficient for the operation can be contained. In relation to the volume of the container part 4, the cross-sectional area of the container part 4 is preferably set at 0.7 to 80 $cm^2$, more preferably 2 to 60 $cm^2$, even more preferably 3 to 40 $cm^2$, further even more preferably 10 to 20 $cm^2$. When the cross-sectional are of the container part 4 is set within this range, the container part 4 is easily clasped, and eventually is easily squeezed. The volume of the hair cosmetic material 3 produced in the container part 4 is preferably from 2 to 200 $cm^3$, more preferably from 20 to 150 $cm^3$, even more preferably from 50 to 135 $cm^3$ in the condition in which the percentage c of the volume of the head space is within the range described above.

In the hair cosmetic article of the present invention, the whole length of the applicator 1 is one of the factors which affect the operability of the applicator 1, or the discharging property of the hair cosmetic material 3. From this viewpoint, the whole length of the applicator 1, i.e., a length from the lowermost part of the applicator to the uppermost part of the applicator in an upright state shown in FIG. 1, is set at preferably 5 to 40 cm, more preferably 10 to 40 cm, even more preferably 15 to 30 cm, further even more preferably 20 to 25 cm.

As described above, when the hair cosmetic material 3 in the present invention includes the compositions A, B and C, or includes the compositions A' and B, the hair cosmetic material 3 has a special characteristic, which is liquid including the powdery component. This powdery component is derived from the composition C or the composition A'. The dispersibility of the powdery component in the hair cosmetic material 3 is one of the factors that influence on the performance of dyeing or bleaching performance of the hair cosmetic material 3. It is very important, accordingly, to mix and uniformly disperse the powdery component. The surface of the powdery component in the composition C or the composition A' including the powdery oxidation assistant is often hydrophobic. It is advantageous, accordingly, that compositions A and B, and the hair cosmetic material 3 are hydrophobic (i.e., a water content is low), in order to improve the mixing or the uniform dispersibility of the powdery component. In particular, when the composition C including the powdery oxidation assistant is used, it is advantageous to previously mix the composition C with the component having a higher hydrophobicity (having a lower water content) among the compositions A and B, from the viewpoint described above. Specifically, a water content in one of the compositions A and B, (the composition B in the case of the composition A') is preferably from 5 to 95% by mass, more preferably from 10 to 75% by mass, even more preferably from 15 to 55% by mass, further even more preferably from 20 to 35% by mass. Furthermore, from the same viewpoint, the water content in the hair cosmetic material 3 is preferably from 5 to 70% by mass, more preferably from 10 to 60% by mass, even more preferably from 20 to 45% by mass.

When the hair cosmetic material 3 used in the present invention includes the compositions A" and B, water and, if necessary, an organic solvent can be used as a medium in either one or both of the compositions A" and B. The organic solvents may include lower alkanols such as ethanol and 2-propanol; aromatic alcohols such as benzyl alcohol and benzyloxyethanol; polyols such as propylene glycol, 1,3-butanediol, diethylene glycol, and glycerin; cellosolves such as ethyl cellosolve, butyl cellosolve, and benzyl cellosolve; and carbitols such as ethyl carbitol and butyl carbitol. In any case in which the organic solvent is contained in either one or both of the compositions A" and B, the organic solvent is contained in a content of preferably 0.01 to 25% by mass, more preferably 0.05 to 15% by mass, even more preferably 0.1 to 10% by mass in the hair cosmetic material.

It is preferable to set pH of the hair cosmetic material 3 at a comparatively high value, because clear operation effects can be obtained. On the contrary, however, the hair easily suffers damage. In order to obtain the clear operation effects, and reduce the damage to the hair, accordingly, it is preferable to set pH of the hair cosmetic material 3 at 8.0 to 12.5, more preferably 8.0 to 11.0, even more preferably 8.0 to 10.5 at 25° C. The pH is measured using, for example, a pH meter F-51 manufactured by HORIBA, Ltd.

The pH of the hair cosmetic material 3 is mainly dominated by the composition A, which is the composition including the alkali agent, and thus in order to set the pH of the hair cosmetic material 3 at the range described above, it is preferable to use a carbonate or a hydrogencarbonate as the alkali agent contained in the composition A, when the hair cosmetic material 3 used in the present invention includes the compositions A, B and C, or includes the compositions A' and B. It is particularly preferable to use ammonium carbonate or ammonium hydrogencarbonate. When the carbonate or hydrogencarbonate is used as the alkali agent, a content of the carbonate or hydrogencarbonate in the total amount of the compositions A, B and C or the total amount of the compositions A' and C is preferably from 0.1 to 10% by mass, more preferably from 0.1 to 8% by mass, even more preferably from 1 to 7% by mass, further even more preferably from 2 to 6% by mass, for inhibiting the damage to the hair, decreasing an amount of ammonia, and inhibiting occurrence of unpleasant odors.

In the composition A and the composition A', an alkali agent which can be used other than the carbonate or hydrogencarbonate include, for example, ammonia, isopropanol amine, monoethanol amine, diethanol amine, triethanol amine, 2-amino-2-methyl-1-propanol, sodium hydroxide, potassium hydroxide, sodium carbonate, sodium silicate, arginine, and the like. The alkali agents may be used alone or as a mixture of two or more kinds.

It is preferable to set the proportion of the alkali agent in the composition A or the composition A' at 1 to 50% by mass, more preferably 1 to 45% by mass, even more preferably 5 to 40% by mass, further even more preferably 10 to 30% by mass. When the proportion of the alkali agent is set within this range, sufficient bleaching effects can be obtained without excessive damage to the hair. Components contained in the composition A other than the alkali agent may include, for example, components which have hitherto been used in the technical filed such as a dye, an oily component, a surfactant, silicones, a polyhydric alcohol and water.

The hair cosmetic material 3 can be used for hair dyeing when a dye is included in the composition A, and can be used for hair bleaching when the dye is not included therein. As the dye, oxidation dye intermediates, direct dyes, and the like can be used. The oxidation dye intermediate can be exemplified by known precursors or couplers which are usually used in hair dye, and the direct dye can be exemplified by well-known acid dyes, basic dye, disperse dyes, reactive dyes, and the like.

When the hair cosmetic material 3 used in the present invention includes the compositions A" and B, the alkali agent contained in the composition A" may include, for example, ammonia, ammonium carbonate, ammonium hydrogencarbonate, isopropanol amine, monoethanol amine, diethanol amine, triethanol amine, 2-amino-2-methyl-1-propanol, sodium hydroxide, potassium hydroxide, sodium carbonate, sodium silicate, arginine, and the like. The alkali agents may be used alone or as a mixture of two or more kinds. Of these, one or more compounds selected from the ammonia, ammonium carbonates and ammonium hydrogencarbonates are preferable in terms of sufficient dyeing effect.

The proportion of the alkali agent in the composition A" is preferably 1 to 50% by mass, more preferably 1.2 to 30% by mass, even more preferably 1.5 to 20% by mass, further even more preferably 2 to 15% by mass. When the proportion of the alkali agent is set within this range, the sufficient dyeing effects can be obtained without excessive damage to the hair.

When the hair cosmetic material 3 used in the present invention includes the compositions A" and B, the composition A" includes a surfactant. The composition B can also include the surfactant. When the surfactant is contained in the composition B, the surfactant may be the same as or different from the surfactant contained in the composition A". In either of a case in which the surfactant is contained only in the composition A" or a case in which the surfactant is contained in both of the compositions A" and B, the surfactant is contained in a content of, preferably 0.1 to 40% by mass, more preferably 0.5 to 30% by mass, even more preferably 1 to 20% by mass in the hair cosmetic material, for improving the discharging property and the applying property of the hair cosmetic material produced by mixing the surfactant, and the compositions A" and B.

Either of an anionic surfactant, a cationic surfactant, amphoteric surfactant and non-ionic surfactant can be used as the surfactant, for improving the discharging property and the applying property of the hair cosmetic material produced by mixing the compositions A" and B. Of these, it is preferable to use the cationic surfactant in combination with the non-ionic surfactant in order to improve the above-mentioned discharging property and applying property.

(Anionic Surfactant)

The anionic surfactant may include sulfuric acid ester surfactants such as alkyl sulfates and alkyl ether sulfates; carboxylic acid surfactants such as fatty acid salts, and salts of alkyl succinate or alkenyl succinate; phosphoric acid ester surfactants such as alkyl phosphates and alkyl ether phosphates; and sulfonic acid surfactants such as salts of sulfosuccinic acid, salts of isethionic acid, taurine salts, alkylbenzene sulfonic acids, α-olefin sulfonic acids, and alkane sulfonic acids, and the like. Preferable examples thereof may include alkyl sulfates and polyoxyalkylene alkyl sulfates; whose alkyl group has preferably 10 to 24, more preferably 12 to 18, carbon atoms, and the alkyl group is preferably linear. In addition, the polyoxyalkylene alkyl sulfates are preferable, and the polyoxyethylene alkyl sulfates are more preferable; especially whose average addition molar number of the oxyethylene group is preferably from 1 to 10, more preferably from 2 to 5. The anionic surfactant is preferably contained in a content of 0.1 to 20% by mass, more preferably 0.5 to 15% by mass in the hair cosmetic material, in order to improve the discharging property and the applying property of the hair cosmetic material produced by mixing the compositions A" and B.

(Cationic Surfactant)

As the cationic surfactant, quaternary ammonium salts with a long-chain monoalkyl are preferable. Examples thereof may include cetrimonium chloride, steartrimonium chloride, behentrimonium chloride, stearalkonium chloride, benzalkonium chloride, and the like, and steartrimonium chloride and behentrimonium chloride are more preferable. Commercially available products of the cationic surfactant may include Quartamin 86 W, Quartamin 86 P Conc, Quartamin 60 W, Quartamin D 2345 P (those are manufactured by Kao Corporation), and Nikkor CA-2580 (Nihon Surfactant Kogyo K. K). The cationic surfactant is preferably contained in a content of 0.1 to 5% by mass, more preferably 0.3 to 3% by mass in the hair cosmetic material, in order to improve the discharging property and the applying property of the hair cosmetic material produced by mixing the compositions A" and B.

(Amphoteric Surfactant)

The amphoteric surfactant may include carbobetaine, amidobetaine, sulfobetaine, hydroxysulfobetaine, amidosulfobetaine, phosphobetaine, and imidazolinium surfactants, having an alkyl, alkenyl or acyl group having 8 to 24 carbon atoms. Of these, the carbobetaine surfactants and the sulfobetaine surfactant are preferable. Preferable amphoteric surfactants may include lauramidopropyl betaine, cocamidopropyl betaine, lauryldimethylaminoacetic acid betaine, laurylhydroxysulfobetaine, and the like. The amphoteric surfactant is preferably contained in a content of 0.1 to 5% by mass in the hair cosmetic material, more preferably 0.3 to 3% by mass, in order to improve the discharging property and the applying property of the hair cosmetic material produced by mixing the compositions A" and B.

(Non-Ionic Surfactant)

The non-ionic surfactant may include alkyl polyglycosides, polyoxyalkylene alkyl ethers, alkyl glyceryl ethers, and the like. The number of carbon atoms of the alkyl group in the alkyl polyglycoside is preferably from 8 to 18, more preferably from 8 to 14, even more preferably from 9 to 11, and this alkyl group is preferably linear. The average degree of condensation of the glycoside is preferably from 1 to 5, more preferably from 1 to 2. The number of carbon atoms of the alkyl group in the polyoxyalkylene alkyl ether is preferably from 10 to 22, more preferably from 12 to 18, and this alkyl group is preferably linear. The polyoxyethylene alkyl ethers are more preferable, and, of these, ethers in which the oxyethylene group has an average addition molar number of 1 to 40 is preferable, more preferably the molar number being from 4 to 30. The alkyl glyceryl ethers whose alkyl group has 8 to 18 carbon atoms are preferable, more preferably the number of carbon atoms being from 8 to 12, and this alkyl group is preferably branched. The non-ionic surfactant is preferably contained in a content of 0.5 to 15% by mass in the hair cosmetic material, more preferably 1 to 10% by mass, in order to improve the discharging property and the applying property of the hair cosmetic material produced by mixing the compositions A" and B.

Regardless of whether the hair cosmetic material 3 used in the present invention includes the compositions A, B and C, the compositions A' and B, or the compositions A" and B, for example, hydrogen peroxide may be used as the oxidizing agent contained in the composition B. The oxidizing agent is preferably contained in an amount of 0.1 to 15% by mass, more preferably 0.5 to 12% by mass, even more preferably 1 to 10% by mass, further even more preferably 5 to 10% by mass in the composition B. When the proportion of the oxidizing agent is set within this range, sufficient dyeing effects and bleaching effects can be obtained without excessive damage to the hair. Components contained in the composition B other than the oxidizing agent may include components which have hitherto been conventionally used in the technical filed such as a poly alcohol, silicones, a surfactant, a stabilizer of hydrogen peroxide, an organic acid or inorganic acid, a pH-controlling agent, and water.

When the hair cosmetic material 3 used in the present invention includes the compositions A, B and C, for example, persulfate such as ammonium persulfate, sodium persulfate or potassium persulfate may be used as the powdery oxidation assistant contained in the composition C. The oxidation assistant is preferably contained in an amount of 10 to 99% by mass, more preferably 20 to 80% by mass, even more preferably 30 to 75% by mass, further even more preferably 40 to 60% by mass in the composition C. When the proportion of the oxidation assistant is set within this range, sufficient bleaching effects can be obtained. Components contained in the composition C other than the oxidation assistant may include components which have hitherto been used in the technical filed other than water, such as an oily component, an alkali agent such as carbonate or hydrogencarbonate, and a pH-controlling agent.

When the hair cosmetic material 3 used in the present invention includes the compositions A' and B, as the composition A', the alkali agent contained in the composition A and the oxidation assistant contained in the composition C, which are described above, are used. It is particularly preferable to use a component including the powdery alkali agent and the powdery oxidation assistant in a powdery state as a whole, in terms of stability.

When the hair cosmetic material 3 used in the present invention includes the compositions A" and B, and is used for hair dyeing, the composition A" includes a dye. The dye may include, for example, oxidation dye intermediates, direct dyes, and the like.

(Oxidation Dye Intermediate)

As the oxidation dye intermediate, precursors and couplers which are used in usual hair dyes may be used. The precursor may include, for example, para-phenylenediamine, toluene-2,5-diamine, ortho-chloro-para-phenylenediamine,N-phenyl para-phenylenediamine,N,N-bis(hydroxyethyl)-para-phenylenediamine, 3-methyl-4-aminophenol, 2-hydroxyethyl-para-phenylenediamine, para-aminophenol, para-methylaminophenol, 4-aminometacresol, ortho-aminophenol, slats thereof, and the like. In addition, the coupler may include, for example, resorcin, 2-methylresorcin, 1-naphthol, 1,5-dihydroxynaphthalene, 5-amino-ortho-cresol, meta-phenylenediamine, orthoaminophenol, meta-aminophenol, para-aminophenol, 2,4-diaminophenoxyethanol, 2,6- diaminopyridine, 2-methyl-5-hydroxyethylaminophenol, 2-amino-3-hydroxypyridine, salts thereof, and the like. Each of the precursor and the coupler may be used as a mixture of two or more kinds, and each of the precursor and the coupler is contained preferably in a content of 0.01 to 5% by mass, more preferably 0.1 to 4% by mass in the composition A", respectively.

(Direct Dye)

The direct dye may include acid dyes, nitro dyes, disperse dyes, basic dyes, and the like. More specifically, the acid dye may include Blue No. 1, Violet No. 401, Black No. 401, Orange No. 205, Red No. 227, Red No. 106, Yellow No. 203, Acid Orange 3, and the like; the nitro dye may include 2-nitro-p-phenylenediamine, 2-amino-6-chloro-4-nitrophenol, 3-nitro-p-hydroxyethylaminophenol, 4-nitro-o-phenylenediamine, 4-amino-3-nitrophenol, 4-hydroxypropylamino-3-nitrophenol, HC Blue 2, HC Orange 1, HC Red 1, HC Yellow 2, HC Yellow 4, HC Yellow 5, HC Red 3, N,N-bis(2-hydroxyethyl)-2-nitro-p-phenylenediamine, and the like; the disperse dye may include Disperse Violet 1, Disperse Blue 1, Disperse Black 9, and the like; and the basic dye may include Basic Blue 99, Basic Brown 16, Basic Brown 17, Basic Red 76, Basic Yellow 76, Basic Orange 31, Basic Red 51, and the like. The direct dye may be used as a mixture of two or more kinds, and may be used in combination with the oxidation dye intermediate. It is preferably contained in a content of 0.001 to 5% by mass, more preferably 0.01 to 3% by mass in the composition A".

When the hair cosmetic material 3 used in the present invention includes the compositions A" and B, an oily agent can be further contained in either one or both of the compositions A" and B, in order to improve the discharging property and the applying property of the hair cosmetic material produced by mixing the compositions A" and B. The oily agent may include hydrocarbons such as squalene, squalane, liquid paraffin, liquid isoparaffin and cycloparaffins; glycerides such as castor oil, cacao seed oil, mink oil, avocado oil, and olive oil; waxes such as beeswax, spermaceti wax, lanolin, and carnauba wax; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate, and tridecyl isononanoate; higher fatty acids such as capric acid, lauric acid, myristic acid, palmitic acid, stearic acid, behenic acid, oleic acid, coconut oil fatty acid, isostearic acid, and isopalmitic acid; higher alcohols such as myristyl alcohol, cetyl alcohol, stearyl alcohol, behenyl alcohol, oleyl alcohol, 2-octyldodecanol, and cetostearyl alcohol; and others such as isostearylglyceryl ether and polyoxypropylenebutyl ether. Of these, the higher alcohols are preferable, and myristyl alcohol, cetyl alcohol, and stearyl alcohol are more preferable. When the oily agent is contained in the compositions A" and B, the oily agent contained in the composition A" and the oily agent contained in the composition B may be the same or different. In either of the case in which the oily agent is added to the composition A" or the composition B and the case in which it is contained in the both compositions, the oily agent is preferably contained in a content of 0.1 to 15% by mass, more preferably 0.5 to 13% by mass, even more preferably 1 to 10% by mass in the hair cosmetic material, in order to improve the discharging property and the applying property of the hair cosmetic material produced by mixing the compositions A" and B.

When the hair cosmetic material 3 used in the present invention includes the compositions N' and B, a cationic polymer can be further contained in either one or both of the compositions A" and B, in order to improve the discharging property and the applying property of the hair cosmetic material produced by mixing the compositions A" and B. The cationic polymer refers to a polymer having a cationic group or a group capable of forming a cationic group by ionization, and includes amphoteric polymers which are cationic as a whole. The cationic polymer includes, therefore, polymers having an amino group or an ammonium group on the side chain of the polymer chain, and water-soluble polymers having a diallyl quaternary ammonium salt as a structural unit, such as cationized cellulose derivatives, cationic starches, cationized guar gum derivatives, polymers or copolymers of a diallyl quaternary ammonium salt, and quaternary polyvinyl pyrrolidone derivatives. Of these, in particular, the polymers having a diallyl quaternary ammonium salt as a structure unit, quaternary polyvinyl pyrrolidone derivatives and cationized cellulose derivatives are preferable, in terms of effect of softness, smoothness and easy passage of fingers while the hair is shampooed, and good coherence and moisture retention while the hair is dried; the polymers or copolymers of a diallyl quaternary ammonium salt, and cationized cellulose derivative are more preferable; and the polymers or copolymers of a diallyl quaternary ammonium salt are even more preferable.

Specific examples of the polymer or copolymer of a diallyl quaternary ammonium salt may include dimethyldiallyl ammonium chloride polymers-(polyquaternium 6, for example, Merquat 100; manufactured by Nalco Company), dimethyldiallyl ammonium chloride/acrylic acid copolymers (polyquaternium 22, for example, Merquat 280, Merquat 295; Nalco Company), dimethyldiallyl ammonium chloride/acrylamide copolymers (polyquaternium 7, for example, Merquat550; Nalco Company), and Merquat 280 and Merquat 295 are preferable.

When the cationic polymer is contained in both of the compositions A" and B, the cationic polymer contained in the composition A" and the cationic polymer contained in the composition B may be the same or different, and the cationic polymers may be used as a mixture of two or more kinds. Although the higher its content, the higher the effects, the polymer is preferably contained in a content of 0.001 to 20% by mass, more preferably 0.01 to 10% by mass, even more preferably 0.05 to 5% by mass in the hair cosmetic material, in any of the case in which the polymer is contained in either the composition A" or the composition B, and the case in which it is contained in both of the compositions A" and B, in terms of the storage stability and the viscosity stability of the agent alone or when the agents are mixed.

When the hair cosmetic material 3 used in the present invention includes the compositions A" and B, a silicone can be further contained in the compositions A" and B, in order to impart a high conditioning effect to the hair. The silicones may include dimethylpolysiloxane, methylphenylpolysiloxane, polyether-modified silicones, amino-modified silicones, oxazoline-modified silicone elastomers, and emulsions in which the silicone described above is dispersed in water with a surfactant. Of these, the polyether-modified silicones, amino-modified silicones, and emulsions thereof are preferable, because they can be stably dispersed in water with using no thickener. When the silicone is contained in both of the compositions A" and B, the silicone contained in the composition A" and the silicone contained in the composition B may be the same or different.

When the silicon is added to the hair cosmetic material in which the composition A" and the composition B are mixed, the content of the silicone is preferably 2% by mass or less, more preferably from 0.005 to 1% by mass, even more preferably from 0.01 to 0.5% by mass in the hair cosmetic material, in any of the case in which the silicone is contained in either the composition A″ or the composition B, and the case in which it is contained in both of the compositions A″ and B, in order to impart the high conditioning effect to the hair.

Regardless of whether the hair cosmetic material 3 used in the present invention includes the compositions A, B and C, the compositions A′ and B, or the compositions A″ and B, components which have been conventionally used in the technical filed may be admixed with any of the compositions for various admixture proposals, in addition to the components described above. The various proposals of the admixture of the components may include promotion of permeation, pearling, preservation, metal sequestering, stabilization, anti-oxidation, ultraviolet absorption, moisture retention, coloring of products, conditioning, thickening, forming, dissolution, addition of perfume, and the like. More specifically, the components may include animal and vegetable fats and oils, natural or synthetic polymers, ethers, anti-oxidants, crude drug extracts, moistening agents, stabilizers, solvents, thickeners, excipients, conditioning agents, higher fatty acids, preservatives, chelating agents, proteins, protein hydrolysates, amino acids, plant extracts, ultraviolet absorbing agents, vitamins, coloring agents, perfumes, and the like. Further more specifically, 8-quinolinol sulfates, EDTA-2 Na, EDTA-4 Na, almond protein, alanine, arginine, isostearylglyceryl, isostearyl glyceryl pentaerythrityl, isopropanol, ethanol, etidronic acid, ethyl paraben, oleic acid, carbon black, chamomile extract, xanthan gum, glycerin, ultramarine blue, diatomaceous earth, corn starch, titanium oxide, silica, stearic acid, calcium stearate, cellulose gum, K sorbate, magnesium carbonate, camellia oil, niacinamide, panthenol, hydroxyethyl cellulose, glyceryl hydroxystearate, fucus vesiculosus extract, propanol, propylene glycol, benzyl alcohol, benzophenone-3, benzophenone-4, polyquaternium-22, polyquaternium-6, polyquatemium-10, mineral oil, myristic acid, methyl paraben, lauric acid, rosemary oil, Chrome yellow, hydrolyzed almond protein, hydrolyzed wheat protein, wheat germ protein, and the like.

When the hair cosmetic material 3 used in the present invention includes the compositions A, B and C, or the compositions A′ and B, the alkali agent is mixed with the total amount of the compositions A, B and C, or the compositions A′ and C in an amount of preferably 0.5 to 30% by mass, more preferably 1 to 25% by mass, even more preferably 5 to 15% by mass, further even more preferably 7 to 9% by mass; the oxidizing agent is mixed with the total amount of the compositions A, B and C, or the compositions A′ and C in an amount of preferably from 1 to 10% by mass, more preferably 2 to 7% by mass, even more preferably 3 to 6% by mass; and the oxidation assistant is mixed with the total amount of the compositions A, B and C, or the compositions A′ and C in an amount of preferably 1 to 40% by mass, more preferably 1 to 30% by mass, even more preferably 1 to 20% by mass, further even more preferably 2 to 10% by mass.

Although the present invention has been explained based on the preferable embodiments, the present invention is not limited to the embodiments described above. For example, in the embodiment described above, the comb teeth 22 of the application part 2 in the applicator 1 are disposed substantially annularly, but the comb teeth 22 may be disposed in a state other than the almost annular state instead thereof, so long as the comb teeth 22 are disposed so as to surround the agent discharge port 21. For example, they may be disposed so that a track drawn by the comb teeth 22 forms an anisotropy shape such as an ellipse or an oval.

The hair cosmetic article in the embodiment described above is a three-component agent having the compositions A, B and C, or a two-component agent having the compositions A′ and B, or the compositions A″ and B, but a composition including an agent for improving feeling such as extracts from animals and plants may be added thereto as a composition D.

With respect to the embodiments described above, the hair cosmetic article, and the hair dyeing or bleaching method of the present invention is further disclosed below.

<1>

A hair cosmetic article comprising:
a composition A including an alkali agent;
a composition B including an oxidizing agent;
a composition C including a powdery oxidation assistant; and
a hair cosmetic applicator including a container part in which a hair cosmetic material produced by mixing the compositions A, B and C and having a viscosity of 3 to 30 Pa·s, preferably 5 to 15 Pa·s, more preferably 7 to 13 Pa·s, even more preferably 8.5 to 13 Pa·s at 30° C. is to be contained; an application part by which the hair cosmetic material is applied to a hair-bundle; and an extension part having a liquid-leading passage which communicates the container part to the application part,
wherein
the application part includes a discharge port and a comb part, and the comb part includes a plurality of comb teeth which are disposed substantially annularly so as to surround the discharge port.

<2>

A hair cosmetic article comprising:
a composition A′ including an alkali agent and a powdery oxidation assistant;
a composition B including an oxidizing agent; and
a hair cosmetic applicator including a container part in which a hair cosmetic material produced by mixing the compositions A, B and C and having a viscosity of 3 to 30 Pa·s, preferably 5 to 15 Pa·s, more preferably 7 to 13 Pa·s, even more preferably 8.5 to 13 Pa·s at 30° C. is to be contained; an application part by which the hair cosmetic material is applied to a hair-bundle; and an extension part having a liquid-leading passage which communicates the container part to the application part,
wherein
the application part includes a discharge port and a comb part, and the comb part includes a plurality of comb teeth which are disposed substantially annularly so as to surround the discharge port.

<3>

The hair cosmetic article according to <1> or <2>, wherein a value of a/b is from 0.1 to 5, preferably from 0.2 to 4, more preferably from 0.3 to 2, even more preferably from 0.4 to 1 wherein a denotes a diameter (mm) of the narrowest part of the liquid-leading passage and b denotes a viscosity (Pa·s) of the hair cosmetic material at 30° C.

<4>

The hair cosmetic article according to any one of <1> to <3>, wherein a value of c/b is from 0.5 to 15, preferably from 0.6 to 13, more preferably from 0.8 to 10, even more preferably from 1 to 7 wherein c denotes a percentage (%) of a volume of a head space to a volume of the container part in the state in which the hair cosmetic material is contained in the container part, and b denotes a viscosity (Pa·s) of the hair cosmetic material at 30° C.

<5>

The hair cosmetic article according to any one of <1> to <4>, wherein the hair cosmetic material is liquid including a powdery component.

<6>

The hair cosmetic article according to any one of <1> to <5>, wherein the hair cosmetic material has a pH of 8 to 12.5, preferably 8.0 to 11.0, more preferably 8.0 to 10.5 at 25° C.

<7>

The hair cosmetic article according to any one of <1> to <6>, wherein the hair cosmetic applicator has a whole length of 5 to 40 cm, preferably 10 to 40, more preferably 15 to 30, even more preferably 20 to 25.

<8>

The hair cosmetic article according to <1>, wherein the composition A may be in the state of liquid, cream, paste, or a powder, preferably in the state of liquid or cream, more preferably in the state of liquid, and the composition A further includes a dye.

<9>

The hair cosmetic article according to <1> or <8>, wherein the composition A includes a carbonate or a hydrogencarbonate as the alkali agent.

<10>

The hair cosmetic article according to <9>, wherein the proportion of the alkali agent in the composition A is preferably 1 to 50% by mass, more preferably 1 to 45% by mass, even more preferably 5 to 40% by mass, further even more preferably 10 to 30% by mass.

<11>

The hair cosmetic article according to <2>, wherein the composition A' may be in the state of liquid, cream, paste, or a powder, preferably in the state of a powder or paste, more preferably in the state of a powder, and the composition A' further includes a dye.

<12>

The hair cosmetic article according to any one of <1> to <11>, wherein the composition B may be in the state of liquid, or cream or paste, preferably in the state of liquid or cream, more preferably in the state of liquid.

<13>

The hair cosmetic article according to claim <12>, wherein the proportion of the oxidizing agent in the composition B is preferably 0.1 to 15% by mass, more preferably 0.5 to 12% by mass, even more preferably 1 to 10% by mass, further even more preferably 5 to 10% by mass.

<14>

The hair cosmetic article according to <1>, wherein the composition C includes a persulfate such as ammonium persulfate, sodium persulfate or potassium persulfate as an oxidation assistant.

<15>

The hair cosmetic article according to <14>, wherein the proportion of the oxidation assistant in the composition C is preferably 10 to 99% by mass, more preferably 20 to 80% by mass, even more preferably 30 to 75% by mass, further even more preferably 40 to 60% by mass.

<16>

The hair cosmetic article according to any one of <1> to <15>, wherein the proportion of the carbonate or hydrogencarbonate in the hair cosmetic material is preferably from 0.1 to 10% by mass, more preferably from 0.1 to 8% by mass, even more preferably from 1 to 7% by mass, further even more preferably from 2 to 6% by mass.

<17>

The hair cosmetic article according to any one of <1> to <16>, wherein the alkali agent is mixed in the hair cosmetic material in an amount of preferably 0.5 to 30% by mass, more preferably 1 to 25% by mass, even more preferably 5 to 15% by mass, further even more preferably 7 to 9% by mass.

<18>

The hair cosmetic article according to any one of <1> to <17>, wherein the oxidizing agent is mixed in the hair cosmetic material in an amount of preferably 1 to 10% by mass, more preferably 2 to 7% by mass, even more preferably 3 to 6% by mass; and the oxidation assistant in the hair cosmetic material is mixed in an amount of preferably 1 to 40% by mass, more preferably 1 to 30% by mass, even more preferably 1 to 20% by mass, further even more preferably 2 to 10% by mass.

<19>

The hair cosmetic article according to any one of <1> to <18>, wherein the proportion of water in the hair cosmetic material is preferably from 5 to 70% by mass, more preferably from 10 to 60% by mass, even more preferably from 20 to 45% by mass.

<20>

The hair cosmetic article according to any one of <1> to <19>, wherein the container part is a double nested container including a container body having a squeezable bottomed cylindrical outer container, and an inner bag which is disposed in the outer container and whose port is air-tightly joined to an inside surface of a cylindrical port of the outer container; and a connection cap having a check valve attached to a neck part of the container body.

<21>

The hair cosmetic article according to any one of <1> to <20>, wherein the diameter a of the liquid-leading passage is preferably from 2 to 50 mm, more preferably from 3 to 30 mm, even more preferably from 3 to 15 mm, further even more preferably from 5 to 10 mm.

<22>

The hair cosmetic article according to <4>, wherein the percentage c of the volume of the head space is preferably from 5 to 90%, more preferably from 10 to 80%, even more preferably from 15 to 70%.

<23>

The hair cosmetic article according to any one of <1> to <22>, wherein the comb tooth has a height of preferably 5 to 30 mm, more preferably 5 to 20 mm, even more preferably 7 to 17 mm;

a circular line which circumscribes a cross-section of a base end part of each of the comb teeth, and passes a center of the cross-section of the base end part of each of the comb teeth has an internal diameter L4 of preferably from 5 to 30 mm, more preferably from 5 to 20 mm, even more preferably from 5 to 15 mm, further even more preferably from 8 to 13 mm; and the comb tooth has a width W of preferably 0.1 to 5 mm, more preferably 0.1 to 3 mm, even more preferably 0.5 to 2.5 mm.

<24>

A hair dyeing or bleaching method using a hair cosmetic article, the hair cosmetic article including:

a composition A including an alkali agent;

a composition B including an oxidizing agent;

a composition C including a powdery oxidation assistant; and a hair cosmetic applicator including a container part in which a hair cosmetic material produced by mixing the compositions A, B and C and having a viscosity of 3 to 30 Pa·s, preferably 5 to 15 Pa·s, more preferably 7 to 13 Pa·s, even more preferably 8.5 to 13 Pa·s at 30° C. is to be included; an application part by which the hair cosmetic material is applied to a hair-bundle; and an extension part having a liquid-leading passage which communicates the container part to the application part, wherein
  the application part includes a discharge port and a comb part, and the comb part includes a plurality of comb teeth which are disposed substantially annularly so as to surround the discharge port,
the method comprising the steps 1) to 3) of:
  1) a step of mixing the compositions A, B and C in the container part to produce the hair cosmetic material in the container part;
  2) a step of supplying the hair cosmetic material to the application part from the container part through the liquid-leading passage in the extension part using the hair cosmetic applicator,
    the hair cosmetic applicator being in the state in which the container part in which the hair cosmetic material is contained, the application part, and the extension part are assembled; and
  3) a step of applying the hair cosmetic material supplied to the application part to hair.

<25>
A hair dyeing or bleaching method using a hair cosmetic article, the hair cosmetic article including:
  a composition A' including an alkali agent and a powdery oxidation assistant;
  a composition B including an oxidizing agent; and
  a hair cosmetic applicator including a container part in which a hair cosmetic material produced by mixing the compositions A' and B and having a viscosity of 3 to 30 Pa·s, preferably 5 to 15 Pa·s, more preferably 7 to 13 Pa·s, even more preferably 8.5 to 13 Pa·s at 30° C. is to be contained; an application part by which the hair cosmetic material is applied to a hair-bundle; and an extension part having a liquid-leading passage which communicates the container part to the application part,
wherein
  the application part includes a discharge port and a comb part, and the comb part includes a plurality of comb teeth which are disposed substantially annularly so as to surround the discharge port,
the method comprising the steps 1) to 3) of:
  1) a step of mixing the compositions A' and B in the container part to produce the hair cosmetic material in the container part;
  2) a step of supplying the hair cosmetic material to the application part from the container part through the liquid-leading passage in the extension part using the hair cosmetic applicator,
    the hair cosmetic applicator being in the state in which the container part in which the hair cosmetic material is contained, the application part, and the extension part are assembled; and
  3) a step of applying the hair cosmetic material supplied to the application part to hair.

<26>
The hair dyeing or bleaching method according to <24>, wherein the compositions A, B and C are put in the container part, then an opening of the container part is closed with a closing member or the extension part, and the compositions A, B and C are mixed in the closed state.

<27>
The hair dyeing or bleaching method according to <24>, wherein the composition A may be in the state of liquid, cream or paste, or a powder, preferably in the state of liquid or cream, more preferably in the state of liquid, and
  the composition A further includes a dye.

<28>
The hair dyeing or bleaching method according to <24> or <27>, wherein the composition A includes a carbonate or a hydrogencarbonate as the alkali agent.

<29>
The hair dyeing or bleaching method according to <28>, wherein the proportion of the alkali agent in the composition A is preferably 1 to 50% by mass, more preferably 1 to 45% by mass, even more preferably 5 to 40% by mass, further even more preferably 10 to 30% by mass.

<30>
The hair dyeing or bleaching method according to <25>, wherein the composition A' may be in the state of liquid, cream or paste, or a powder, preferably in the state of a powder or paste, more preferably in the state of a powder, and
  the composition A' further includes a dye.

<31>
The hair dyeing or bleaching method according to any one of <24> to <30>, wherein the composition B may be in the state of liquid, or cream or paste, preferably liquid or cream, more preferably liquid.

<32>
The hair dyeing or bleaching method according to <31>, wherein the proportion of the oxidizing agent in the composition B is preferably 0.1 to 15% by mass, more preferably 0.5 to 12% by mass, even more preferably 1 to 10% by mass, further even more preferably 5 to 10% by mass.

<33>
The hair dyeing or bleaching method according to any one of <24> to <32>, wherein the composition C includes a persulfate such as ammonium persulfate, sodium persulfate or potassium persulfate as the oxidation assistant.

<34>
The hair dyeing or bleaching method according to <33>, wherein the proportion of the oxidation assistant in the composition C is preferably 10 to 99% by mass, more preferably 20 to 80% by mass, even more preferably 30 to 75% by mass, further even more preferably 40 to 60% by mass.

<35>
The hair dyeing or bleaching method according to any one of <24> to <34>, wherein the proportion of the carbonate or hydrogencarbonate in the hair cosmetic material is preferably from 0.1 to 10% by mass, more preferably from 0.1 to 8% by mass, even more preferably from 1 to 7% by mass, further even more preferably from 2 to 6% by mass.

<36>
The hair dyeing or bleaching method according to any one of <24> to <35>, wherein the alkali agent is mixed in the hair cosmetic material in an amount of preferably 0.5 to 30% by mass, more preferably 1 to 25% by mass, even more preferably 5 to 15% by mass, further even more preferably 7 to 9% by mass.

<37>
The hair dyeing or bleaching method according to any one of <24> to <36>, wherein the oxidizing agent is mixed in the hair cosmetic material in an amount of preferably 1 to 10% by mass, more preferably 2 to 7% by mass, even more preferably 3 to 6% by mass; and the oxidation assistant is mixed in the hair cosmetic material in an amount of preferably 1 to 40% by mass, more preferably 1 to 30% by mass, even more preferably 1 to 20% by mass, further even more preferably 2 to 10% by mass.

<38>
The hair dyeing or bleaching method according to any one of <24> to <37>, wherein the proportion of water in the hair cosmetic material is preferably from 5 to 70% by mass, more preferably from 10 to 60% by mass, even more preferably from 20 to 45% by mass.

<39>

The hair dyeing or bleaching method according to any one of <24> to <38>, wherein the container part is a double nested container including a container body having a squeezable bottomed cylindrical outer container, and an inner bag, which is disposed in the outer container and whose port is air-tightly joined to an inside surface of a cylindrical port of the outer container; and a connection cap having a check valve attached to a neck part of the container body.

<40>

The hair dyeing or bleaching method according to any one of <24> to <39>, wherein the diameter a of the liquid-leading passage is preferably from 2 to 50 mm, more preferably from 3 to 30 mm, even more preferably from 3 to 15 mm, further even more preferably from 5 to 10 mm.

<41>

The hair dyeing or bleaching method according to any one of <24> to <40>, wherein
the comb tooth has a height of preferably 5 to 30 mm, more preferably 5 to 20 mm, even more preferably 7 to 17 mm;
a circular line which circumscribes a cross-section of a base end part of each of the comb teeth, and passes a center of the cross-section of the base end part of each of the comb teeth has an internal diameter L4 of preferably from 5 to 30 mm, more preferably from 5 to 20 mm, even more preferably from 5 to 15 mm, further even more preferably from 8 to 13 mm; and
the comb tooth has a width W of preferably 0.1 to 5 mm, more preferably 0.1 to 3 mm, even more preferably 0.5 to 2.5 mm.

<42>

A hair cosmetic article comprising:
a composition A including an alkali agent;
a composition B including an oxidizing agent;
a composition C including a powdery oxidation assistant; and
a hair cosmetic applicator including a container part in which a hair cosmetic material produced by mixing the compositions A, B and C and having a viscosity of 3 to 30 Pa·s, preferably 5 to 15 Pa·s, more preferably 7 to 13 Pa·s, even more preferably 8.5 to 13 Pa·s at 30° C. is to be contained; an application part by which the hair cosmetic material is applied to a hair-bundle; and an extension part having a liquid-leading passage which communicates the container part to the application part,
wherein
the hair cosmetic material has a pH of 8 to 12.5, preferably 8.0 to 11.0, more preferably 8.0 to 10.5 at 25° C.;
a value of a/b is from 0.1 to 5 wherein a denotes a diameter (mm) of the narrowest part of the liquid-leading passage and b denotes a viscosity (Pa·s) of the hair cosmetic material, preferably from 0.2 to 4, more preferably from 0.3 to 2, even more preferably from 0.4 to 11 at 30° C.;
a value of c/b is from 0.5 to 15 wherein c at 30° C. a percentage (%) of a volume of a head space to a volume of the container part in the state in which the hair cosmetic material is contained in the container part, preferably from 0.6 to 13, more preferably from 0.8 to 10, even more preferably from 1 to 7; and
the hair cosmetic applicator has a whole length of 5 to 40 cm, preferably from 10 to 40 cm, more preferably from 15 to 30 cm, even more preferably from 20 to 25 cm.

<43>

A hair cosmetic article including:
a composition A' including an alkali agent and a powdery oxidation assistant;
a composition B including an oxidizing agent; and
a hair cosmetic applicator including a container part in which a hair cosmetic material produced by mixing the compositions A' and B and having a viscosity of 3 to 30 Pa·s, preferably 5 to 15 Pa·s, more preferably 7 to 13 Pa·s, even more preferably 8.5 to 13 Pa·s at 30° C. is to be contained; an application part by which the hair cosmetic material is applied to a hair-bundle, and an extension part having a liquid-leading passage which communicates the container part to the application part,
wherein
the hair cosmetic material has a pH of 8.0 to 12.5, preferably 8.0 to 11.0, more preferably 8.0 to 10.5 at 25° C.,
a value of a/b is from 0.1 to 5, preferably from 0.2 to 4, more preferably from 0.3 to 2, even more preferably from 0.4 to 1 wherein a denotes a diameter (mm) of the narrowest part of the liquid-leading passage, and b denotes a viscosity (Pa·s) of the hair cosmetic material at 30° C.,
a value of c/b is from 0.5 to 15, preferably from 0.6 to 13, more preferably from 0.8 to 10, even more preferably from 1 to 7 wherein c denotes a percentage (%) of a volume of a head space in the container part in the state in which the hair cosmetic material is contained in the container part, to the volume of the container, and
the hair cosmetic applicator has a whole length of 5 to 40 cm, preferably 10 to 40 cm, more preferably 15 to 30 cm, even more preferably 20 to 25 cm.

<44>

The hair cosmetic article according to <42> or <43>, wherein the application part includes a discharge port and a comb part, and the comb part includes a plurality of comb teeth which are disposed so as to surround the discharge port.

<45>

The hair cosmetic article according to <44>, wherein the comb teeth are disposed substantially annularly.

<46>

The hair cosmetic article according to <42>, wherein the composition A may be in the state of liquid, cream or paste, or a powder, preferably in the state of liquid or cream, more preferably in the state of liquid, and
the composition A further includes a dye.

<47>

The hair cosmetic article according to <42> or <46>, wherein the composition A includes a carbonate or a hydrogencarbonate as the alkali agent.

<48>

The hair cosmetic article according to <47>, wherein the proportion of the alkali agent in the composition A is preferably 1 to 50% by mass, more preferably 1 to 45% by mass, even more preferably 5 to 40% by mass, further even more preferably 10 to 30% by mass.

<49>

The hair cosmetic article according to <43>, wherein the composition A' may be in the state of liquid, cream, r paste, or a powder, preferably in the state of a powder or paste, more preferably in the state of a powder, and
the composition A' further includes a dye.

<50>

The hair cosmetic article according to any one of <42> to <49>, wherein the composition B may be in the state of liquid, cream or paste, preferably in the state of liquid or cream, more preferably in the state of liquid.

<51>
The hair cosmetic article according to <50>, wherein the proportion of the oxidizing agent in the composition B is preferably 0.1 to 15% by mass, more preferably 0.5 to 12% by mass, even more preferably 1 to 10% by mass, further even more preferably 5 to 10% by mass.

<52>
The hair cosmetic article according to <42>, wherein the composition C includes a persulfate such as ammonium persulfate, sodium persulfate or potassium persulfate as an oxidation assistant.

<53>
The hair cosmetic article according to <52>, wherein the proportion of the oxidation assistant in the composition C is preferably 10 to 99% by mass, more preferably 20 to 80% by mass, even more preferably 30 to 75% by mass, further even more preferably 40 to 60% by mass.

<54>
The hair cosmetic article according to any one of <42> to <53>, wherein the proportion of the carbonate or hydrogencarbonate in the hair cosmetic material is preferably from 0.1 to 10% by mass, more preferably from 0.1 to 8% by mass, even more preferably from 1 to 7% by mass, further even more preferably from 2 to 6% by mass.

<55>
The hair cosmetic article according to any one of <42> to <54>, wherein the alkali agent is mixed in the hair cosmetic material in an amount of preferably 0.5 to 30% by mass, more preferably 1 to 25% by mass, even more preferably 5 to 15% by mass, further even more preferably 7 to 9% by mass.

<56>
The hair cosmetic article according to any one of <42> to <55>, wherein the oxidizing agent is mixed in the hair cosmetic material in an amount of preferably 1 to 10% by mass, more preferably 2 to 7% by mass, even more preferably 3 to 6% by mass; and the oxidation assistant is mixed in the hair cosmetic material in an amount of preferably 1 to 40% by mass, more preferably 1 to 30% by mass, even more preferably 1 to 20% by mass, further even more preferably 2 to 10% by mass.

<57>
The hair cosmetic article according to any one of <42> to <56>, wherein the proportion of water in the hair cosmetic material is preferably from 5 to 70% by mass, more preferably from 10 to 60% by mass, even more preferably from 20 to 45% by mass.

<58>
The hair cosmetic article according to any one of <42> to <57>, wherein the container part is a double nested container including a container body having a squeezable bottomed cylindrical outer container, and an inner bag, which is disposed in the outer container and whose port is air-tightly joined to an inside surface of a cylindrical port of the outer container; and a connection cap with a check valve attached to a neck part of the container body.

<59>
The hair cosmetic article according to any one of <42> to <58>, wherein the diameter a of the liquid-leading passage is preferably from 2 to 50 mm, more preferably from 3 to 30 mm, even more preferably from 3 to 15 mm, further even more preferably from 5 to 10 mm.

<60>
The hair cosmetic article according to any one of <42> to <59>, wherein a percentage c of a volume of the head space is preferably from 5 to 90%, more preferably from 10 to 80%, even more preferably from 15 to 70%.

<61>
The hair cosmetic article according to <44> or <45>,
wherein the comb tooth has a height of preferably 5 to 30 mm, more preferably 5 to 20 mm, even more preferably 7 to 17 mm;
a circular line which circumscribes a cross-section of a base end part of each of the comb teeth, and passes a center of the cross-section of the base end part of each of the comb teeth has an internal diameter L4 of preferably from 5 to 30 mm, more preferably from 5 to 20 mm, even more preferably from 5 to 15 mm, further even more preferably from 8 to 13 mm; and
the comb tooth has a width W of preferably 0.1 to 5 mm, more preferably 0.1 to 3 mm, even more preferably 0.5 to 2.5 mm <62>
A hair cosmetic article including:
a composition A" including an alkali agent and a surfactant;
a composition B including an oxidizing agent; and
a hair cosmetic applicator including a container part in which a hair cosmetic material produced by mixing the compositions A" and B and having a viscosity of 3 to 30 Pa·s at 30° C., preferably 5 to 15 Pa·s, more preferably 7 to 13 Pa·s, even more preferably 8.5 to 13 Pa·s is to be included; an application part by which the hair cosmetic material is applied to a hair-bundle; and an extension part having a liquid-leading passage which communicates the container part to the application part,
wherein
the application part includes a discharge port and a comb part, and the comb part includes a plurality of comb teeth which are disposed substantially annularly so as to surround the discharge port.

<63>
The hair cosmetic article according to <62>, wherein a value of a/b is from 0.1 to 5, preferably from 0.2 to 4, more preferably from 0.3 to 2, even more preferably from 0.4 to 1, wherein a denotes a diameter (mm) of the narrowest part of the liquid-leading passage and b denotes a viscosity (Pa·s) of the hair cosmetic material.

<64>
The hair cosmetic article according to <62> or <63>, wherein a value of c/b is from 0.5 to 15, preferably from 0.6 to 13, more preferably from 0.8 to 10, even more preferably from 1 to 7, wherein c denotes a percentage (%) of a volume of a head space to a volume of the container part in the state in which the hair cosmetic material is contained in the container part, and b denotes a viscosity (Pa·s) of the hair cosmetic material at 30° C.

<65>
The hair cosmetic article according to any one of <62> to <64>, wherein the hair cosmetic material has a pH of 8.0 to 12.5, preferably 8.0 to 11.0, more preferably 8.0 to 10.5 at 25° C.

<66>
The hair cosmetic article according to any one of <62> to <65>, wherein the hair cosmetic applicator has a whole length of 5 to 40 cm, preferably from 10 to 40 cm, more preferably from 15 to 30 cm, even more preferably from 20 to 25 cm.

<67>
The hair cosmetic article according to any one of <62> to <66>, wherein the composition A" further includes a dye.

<68>
The hair cosmetic article according to any one of <62> to <67>, wherein the surfactant is contained in the hair cosmetic material in an amount of 0.1 to 40% by mass, preferably 0.5 to 30% by mass, more preferably 1 to 20% by mass.

<69>

The hair cosmetic article according to any one of <62> to <68>, wherein the surfactant includes a cationic surfactant and a non-ionic surfactant.

<70>

The hair cosmetic article according to any one of <62> to <69>, wherein the hair cosmetic material includes an oily agent.

<71>

The hair cosmetic article according to any one of <62> to <70>, wherein the hair cosmetic material further includes a cationic polymer.

<72>

The hair cosmetic article according to any one of <62> to <71>, wherein the hair cosmetic material further includes a silicone.

<73>

The hair cosmetic article according to any one of <62> to <72>, wherein the composition A" may be in the state of liquid, cream or paste, or a powder, preferably liquid or cream, more preferably liquid.

<74>

The hair cosmetic article according to any one of <62> to <73>, wherein the composition A" includes a carbonate or a hydrogencarbonate as the alkali agent.

<75>

The hair cosmetic article according to <74>, wherein the proportion of the alkali agent in the composition A" is preferably 1 to 50% by mass, more preferably 1.2 to 30% by mass, even more preferably 1.5 to 20% by mass, further even more preferably 2 to 15% by mass.

<76>

The hair cosmetic article according to any one of <62> to <75>, wherein the composition B may be in the state of liquid or cream or paste, preferably liquid or cream, more preferably liquid.

<77>

The hair cosmetic article according to any one of <62> to <76>, wherein the proportion of the oxidizing agent in the composition B is preferably 0.1 to 15% by mass, more preferably 0.5 to 12% by mass, even more preferably 1 to 10% by mass, further even more preferably 5 to 10% by mass.

<78>

The hair cosmetic article according to any one of <62> to <77>, wherein the container part is a double nested container including a container body having a squeezable bottomed cylindrical outer container, and an inner bag, which is disposed in the outer container and whose port is air-tightly joined to an inside surface of a cylindrical port of the outer container; and a connection cap having a check valve attached to a neck part of the container body.

<79>

The hair cosmetic article according to any one of <62> to <78>, wherein the diameter a of the liquid-leading passage is preferably from 2 to 50 mm, more preferably from 3 to 30 mm, even more preferably from 3 to 15 mm, further even more preferably from 5 to 10 mm.

<80>

The hair cosmetic article according to <64>, wherein the percentage c of the volume of the head space is preferably from 5 to 90%, more preferably from 10 to 80%, even more preferably from 15 to 70%.

<81>

The hair cosmetic article according to any one of <62> to <80>,
wherein the comb tooth has a height of preferably 5 to 30 mm, more preferably 5 to 20 mm, even more preferably 7 to 17 mm;
a circular line which circumscribes a cross-section of a base end part of each of the comb teeth, and passes a center of the cross-section of the base end part of each of the comb teeth has an internal diameter L4 of preferably from 5 to 30 mm, more preferably from 5 to 20 mm, even more preferably from 5 to 15 mm, further even more preferably from 8 to 13 mm; and
the comb tooth has a width W of preferably 0.1 to 5 mm, more preferably 0.1 to 3 mm, even more preferably 0.5 to 2.5 mm.

<82>

A hair dyeing or bleaching method using a hair cosmetic article, the hair cosmetic article including:
a composition A" including an alkali agent and a surfactant;
a composition B including an oxidizing agent; and
a hair cosmetic applicator including a container part in which a hair cosmetic material produced by mixing the compositions A" and B and having a viscosity of 3 to 30 Pa·s, preferably 5 to 15 Pa·s, more preferably 7 to 13 Pa·s, even more preferably 8.5 to 13 Pa·s at 30° C. is to be contained; an application part by which the hair cosmetic material is applied to a hair-bundle; and an extension part having a liquid-leading passage which communicates the container part to the application part,
wherein
the application part includes a discharge port and a comb part, and the comb part includes a plurality of comb teeth which are disposed substantially annularly so as to surround the discharge port,
the method comprising the steps 1) to 3) of
1) a step of mixing the compositions A" and B in the container part to produce the hair cosmetic material in the container part;
2) a step of supplying the hair cosmetic material to the application part from the container part through the liquid-leading passage in the extension part using the hair cosmetic applicator in the state in which the container part in which the hair cosmetic material is contained, the application part, and the extension part are assembled; and
3) a step of applying the hair cosmetic material supplied to the application part to hair.

<83>

The hair dyeing or bleaching method according to <82>, wherein the compositions A" and B are put in the container part, then an opening of the container part is closed with a closing member or the extension part, and the compositions A" and B are mixed in the closed state.

<84>

The hair dyeing or bleaching method according to <82> or <83>, wherein the composition A" further includes a dye.

<85>

The hair dyeing or bleaching method according to any one of <82> to <84>, wherein the surfactant is contained in the hair cosmetic material in an amount of 0.1 to 40% by mass, preferably 0.5 to 30% by mass, more preferably 1 to 20% by mass.

<86>
The hair dyeing or bleaching method according to any one of <82> to <85> wherein the surfactant includes a cationic surfactant and a non-ionic surfactant.
<87>
The hair dyeing or bleaching method according to any one of <82> to <86>, wherein the hair cosmetic material includes an oily agent.
<88>
The hair dyeing or bleaching method according to any one of <82> to <87>, wherein the hair cosmetic material includes a cationic polymer.
<89>
The hair dyeing or bleaching method according to any one of <82> to <88>, wherein the hair cosmetic material includes a silicone.
<90>
The hair dyeing or bleaching method according to any one of <82> to <89>, wherein the composition A" may be in the state of liquid, cream or paste, or a powder, preferably liquid or cream, more preferably liquid.
<91>
The hair dyeing or bleaching method according to any one of <82> to <90>, wherein the composition A" includes a carbonate or a hydrogencarbonate as the alkali agent.
<92>
The hair dyeing or bleaching method according to <91>, wherein the proportion of the alkali agent in the composition A" is preferably 1 to 50% by mass, more preferably 1.2 to 30% by mass, even more preferably 1.5 to 20% by mass, further even more preferably 2 to 15% by mass.
<93>
The hair dyeing or bleaching method according to any one of <82> to <92>, wherein the composition B may be in the state of liquid, or cream or paste, preferably liquid or cream, more preferably liquid.
<94>
The hair dyeing or bleaching method according to any one of <82> to <93>, wherein the proportion of the oxidizing agent in the composition B is preferably 0.1 to 15% by mass, more preferably 0.5 to 12% by mass, even more preferably 1 to 10% by mass, further even more preferably 5 to 10% by mass.
<95>
The hair dyeing or bleaching method according to any one of <82> to <94>, wherein the container part is a double nested container including a container body having a squeezable bottomed cylindrical outer container, and an inner bag, which is disposed in the outer container and whose port is air-tightly joined to an inside surface of a cylindrical port of the outer container; and a connection cap with a check valve attached to a neck part of the container body.
<96>
The hair dyeing or bleaching method according to any one of <82> to <95>, wherein the diameter a of the liquid-leading passage is preferably from 2 to 50 mm, more preferably from 3 to 30 mm, even more preferably from 3 to 15 mm, further even more preferably from 5 to 10 mm.
<97>
The hair dyeing or bleaching method according to any one of <82> to <96>, wherein a percentage c of a volume of a head space is preferably from 5 to 90%, more preferably from 10 to 80%, even more preferably from 15 to 70%, wherein c denotes a percentage (%) of a volume of a head space to a volume of the container part in the state in which the hair cosmetic material is contained in the container part.

<98>
The hair dyeing or bleaching method according to any one of <82> to <97>,
wherein the comb tooth has a height of preferably 5 to 30 mm, more preferably 5 to 20 mm, even more preferably 7 to 17 mm;
a circular line which circumscribes a cross-section of a base end part of each of the comb teeth, and passes a center of the cross-section of the base end part of each of the comb teeth has an internal diameter L4 of preferably from 5 to 30 mm, more preferably from 5 to 20 mm, even more preferably from 5 to 15 mm, further even more preferably from 8 to 13 mm; and
the comb tooth has a width W of preferably 0.1 to 5 mm, more preferably 0.1 to 3 mm, even more preferably 0.5 to 2.5 mm.

EXAMPLES

The present invention is explained in more detailed by means of Examples below, but the scope of the present invention is not limited to such Examples.

Example 1-1

Compositions A, B and C having formulations shown in Tables 1 to 3 were prepared. Each composition was independently contained in a separate container. A container used for containing the composition A was a bottle having a volume of 37 cm$^3$, and 35 g of the composition A was contained therein. A container used for containing the composition B was a bottle having a volume of 149 cm$^3$, and 50 g of the composition B was contain therein. The bottle containing the composition B had the same shape and structure as the container part shown by reference sign 4 in FIG. 1, and was a resin bottle having a double nested structure with a squeezable bottomed cylindrical outer container and an inner bag which was disposed in the outer container and whose port was air-tightly joined to an inside surface of a cylindrical port of the outer container. In a lightproof and gas barrier pouch was contained 15 g of the composition C.

The pouch containing the composition C was opened, and the composition C was added to the bottle containing the composition B. The bottle was closed, and it was shaken in the closed state to promote the mixing. Next, the bottle containing the composition A was opened, and the composition A was added to the bottle in which the compositions B and the C were mixed. The bottle was closed again, and the bottle was shaken in the closed state again to promote the mixing of the compositions A, B and C. The compositions A, B and C were thoroughly mixed as described above to produce a hair cosmetic material. A percentage of a volume of a head space to the volume of the bottle was as shown in Table 1 at that time. The obtained hair cosmetic material 3 was liquid including a powdery component. The viscosity and the pH of the hair cosmetic material 3 at 30° C. were values shown in Table 1.

Next, the bottle containing the hair cosmetic material 3 was opened, and a member, in which the connection cap 45, the extension part 5 and the application part 2 shown in FIG. 1 were combined, was attached to the opening of the bottle to obtain the applicator 1 shown in FIG. 1. The sizes of the extension part 5, the application part 2 and the container part 4 are shown in Table 1.

The container part 4 was clasped and squeezed, thereby supplying the hair cosmetic material 3 to application part 2 from the container part 4 through the extension part 5, and the hair cosmetic material was retained in an area surrounded by multiple comb teeth 22 of the application part 2. The application part 2 was put on a base part of hair of a mannequin head, and the application part was moved in the direction of hair ends to apply the hair cosmetic material 3 to the hair. At this time, if the hair cosmetic material 3 could not be applied up to the hair ends because the hair cosmetic material 3 retained in the application part 2 was finished up in the middle of the application, the application was performed while the container part 4 was lightly squeezed during the application to supply the hair cosmetic material 3 to the application part.

The operation described above was performed by 10 panelists, who had rich experience in hair dyeing and bleaching operations, and evaluations of whether or not the hair cosmetic article was acceptable as a product for mass consumption in items of easiness of mixing of the each composition, and easiness of discharge, application and extension, and difficulty of dripping of the hair cosmetic material 3, were performed by them. When 8 or more panelists among the 10 panelists evaluated that it was acceptable, the article was recorded as an acceptable product. The results are shown in Table 4.

Examples 1-2 to 1-5

Hair cosmetic articles were obtained in the same manner as in Example 1-1 except that conditions shown in Tables 1 to 4 were used. The obtained hair cosmetic articles were evaluated in the same manner as in Example 1-1. The results are shown in table 4.

TABLE 1

| | | Formulation (% by mass) | Example 1-1 | Example 1-2 | Example 1-3 | Example 1-4 | Example 1-5 |
|---|---|---|---|---|---|---|---|
| Composition A | Alkali agent | 28% aqueous ammonia | 8.00 | 8.00 | 8.00 | 8.00 | 8.00 |
| | Other components | ammonium hydrogencarbonate | 14.00 | 14.00 | 14.00 | 14.00 | 14.00 |
| | | Niacinamide | 3.00 | 3.00 | 3.00 | 3.00 | 3.00 |
| | | Methyl paraben | 0.10 | 0.10 | 0.10 | 0.10 | 0.10 |
| | | Etidronic acid | 0.60 | 0.60 | 0.60 | 0.60 | 0.60 |
| | | Chamomile extract | 0.04 | 0.04 | 0.04 | 0.04 | 0.04 |
| | | Water | Balance | Balance | Balance | Balance | Balance |

TABLE 2

| | | Formulation (% by mass) | Example 1-1 | Example 1-2 | Example 1-3 | Example 1-4 | Example 1-5 |
|---|---|---|---|---|---|---|---|
| Composition B | Oxidizing agent | Hydrogen peroxide | 9.00 | 9.00 | 9.00 | 9.00 | 9.00 |
| | Surfactant | Octyldodeceth-25 | 14.00 | 11.00 | 15.00 | 0.00 | 0.00 |
| | | Octyldodeceth-20 | 0.00 | 0.00 | 0.00 | 9.90 | 9.90 |
| | | Oleth-9 | 7.83 | 7.83 | 7.83 | 7.83 | 7.83 |
| | | (C12-14)s-pareth-3 | 13.05 | 13.05 | 13.05 | 13.0 | 13.05 |
| | | Steartrimonium chloride | 1.70 | 1.70 | 1.70 | 1.70 | 1.70 |
| | pH-controlling agent | Phosphoric acid | 0.00 | 0.47 | 0.47 | 0.47 | 0.47 |
| | | Sodium hydroxide | 2.35 | 0.00 | 0.00 | 0.00 | 0.00 |
| | Other components | Isostearyl glyceryl | 1.45 | 1.45 | 1.45 | 1.45 | 1.45 |
| | | Isostearyl glyceryl pentaerythrityl | 3.87 | 3.87 | 3.87 | 3.87 | 3.87 |
| | | Propylene glycol | 11.25 | 11.25 | 11.25 | 11.25 | 11.25 |
| | | Isopropanol | 0.78 | 0.78 | 0.78 | 0.78 | 0.78 |
| | | Ethanol | 10.40 | 10.40 | 10.40 | 10.40 | 10.40 |
| | | Etidronic acid | 0.66 | 0.04 | 0.04 | 0.00 | 0.00 |
| | | 8-Quinolinol sulfate | 0.04 | 0.04 | 0.04 | 0.04 | 0.04 |
| | | Perfume | 0.50 | 0.50 | 0.50 | 0.50 | 0.50 |
| | | Water | Balance | Balance | Balance | Balance | Balance |

TABLE 3

| | | Formulation (% by mass) | Example 1-1 | Example 1-2 | Example 1-3 | Example 1-4 | Example 1-5 |
|---|---|---|---|---|---|---|---|
| Composition C | oxidation assistant | Potassium persulfate | 35.00 | 35.00 | 35.00 | 35.00 | 35.00 |
| | | Ammonium persulfate | 10.00 | 10.00 | 10.00 | 10.00 | 10.00 |
| | Alkali agent | Anhydrous sodium meta-silicate | 9.70 | 9.70 | 9.70 | 9.70 | 9.70 |
| | | Sodium carbonate | 0.90 | 0.90 | 0.90 | 0.90 | 0.90 |

TABLE 3-continued

|   |   | Formulation (% by mass) | Example 1-1 | Example 1-2 | Example 1-3 | Example 1-4 | Example 1-5 |
|---|---|---|---|---|---|---|---|
|   | pH-controlling agent | Ammonium chloride | 1.00 | 1.00 | 1.00 | 1.00 | 1.00 |
|   |   | Ammonium secondary phosphate | 2.00 | 2.00 | 2.00 | 2.00 | 2.00 |
|   | Other components | Cellulose gum | 2.56 | 2.56 | 2.56 | 2.56 | 2.56 |
|   |   | Xanthan gum | 0.18 | 0.18 | 0.18 | 0.18 | 0.18 |
|   |   | Cornstarch | 3.60 | 3.60 | 3.60 | 3.60 | 3.60 |
|   |   | Silica | 2.00 | 2.00 | 2.00 | 2.00 | 2.00 |
|   |   | Diatomaceous earth | 18.34 | 18.34 | 18.34 | 18.34 | 18.34 |
|   |   | Titanium oxide | 3.00 | 3.00 | 3.00 | 3.00 | 3.00 |
|   |   | Mineral oil | 9.20 | 9.20 | 9.20 | 9.20 | 9.20 |
|   |   | Polyquaternium-10 | 0.10 | 0.10 | 0.10 | 0.10 | 0.10 |
|   |   | EDTA-4Na | 2.00 | 2.00 | 2.00 | 2.00 | 2.00 |
|   |   | Ultramarine blue | 0.12 | 0.12 | 0.12 | 0.12 | 0.12 |
|   |   | Perfume | 0.30 | 0.30 | 0.30 | 0.30 | 0.30 |

TABLE 4

|   |   | Example 1-1 | Example 1-2 | Example 1-3 | Example 1-4 | Example 1-5 |
|---|---|---|---|---|---|---|
| Hair cosmetic material 3 | Mass ratio of mixture (A/B/C) | 35/50/15 | 35/50/15 | 35/50/15 | 20/60/20 | 28/52/20 |
|   | Mass (g) | 100 | 100 | 100 | 100 | 100 |
|   | Viscosity of hair cosmetic material (Pa·s) | 10 | 8 | 13 | 4 | 17 |
|   | pH of hair cosmetic material | 9.1 | 9.3 | 9.3 | 9.3 | 9.3 |
| Container part 4 | Volume (cm$^3$) | 149 | 149 | 149 | 149 | 149 |
|   | Minimum cross-section (cm$^2$) | 1.5 | 1.5 | 1.5 | 1.5 | 1.5 |
|   | Maximum cross-section (cm$^2$) | 20 | 20 | 20 | 20 | 20 |
|   | Structure | Outer container/inner bag | Outer container/inner bag | Outer container/inner bag | Outer container/inner bag | Outer container/inner bag |
|   | Percentage of head space to the volume (%) | 33.7 | 30.3 | 30.3 | 29.3 | 29.3 |
| Agent application part 2 | Height of teeth comb 22 (mm) | 15 | 15 | 15 | 15 | 15 |
|   | Number of teeth comb 22 | 15 | 15 | 15 | 15 | 15 |
|   | Width of teeth comb 22 (mm) | 2 | 2 | 2 | 2 | 2 |
|   | Diameter L4 of circle (mm) | 12 | 12 | 12 | 12 | 12 |
| Diameter of liquid-leading passage 51 (mm) |   | 7.5 | 7.5 | 7.5 | 7.5 | 7.5 |
| Whole length of applicator 1 (cm) |   | 25 | 25 | 25 | 25 | 25 |
| Diameter of liquid-leading passage (mm)/viscosity of hair cosmetic material (Pa·s) |   | 0.75 | 0.93 | 0.6 | 1.87 | 0.43 |
| Percentage of head space (%)/viscosity of hair cosmetic material (Pa·s) |   | 3.37 | 3.75 | 2.41 | 7.31 | 1.7 |
| Evaluation | Easiness of mixing | Acceptable (10/10) | Acceptable (10/10) | Acceptable (10/10) | Acceptable (10/10) | Acceptable (10/10) |
|   | Easiness of discharge | Acceptable (10/10) | Acceptable (10/10) | Acceptable (10/10) | Acceptable (10/10) | Acceptable (9/10) |
|   | Easiness of application | Acceptable (10/10) | Acceptable (10/10) | Acceptable (10/10) | Acceptable (9/10) | Acceptable (8/10) |
|   | Easiness of extension | Acceptable (10/10) | Acceptable (10/10) | Acceptable (9/10) | Acceptable (10/10) | Acceptable (8/10) |
|   | Difficulty of dripping | Acceptable (10/10) | Acceptable (9/10) | Acceptable (10/10) | Acceptable (8/10) | Acceptable (10/10) |

As apparent from the results shown in Table 4, it is found that the compositions are easily mixed in the hair cosmetic article of each Example. It is also found that the hair cosmetic material 3 can be easily discharged and applied. Furthermore, it is found that it is easy to extend the hair cosmetic material 3, and is difficult to drip it during the application operation of the hair cosmetic material 3.

Example 1-6

Compositions A, B and C shown in Tables 5 to 8 were prepared. Application of a hair cosmetic material was performed in the same manner as in Example 1-1 except that the compositions as above were used. The application operation was performed by 10 panelists, who had rich experience in hair dyeing and bleaching operations, and easiness of discharge of the hair cosmetic material form the container, easiness of retention of the hair cosmetic material in the application part, and easiness of application of the hair cosmetic material were evaluated by them. The evaluation methods are described below. The results are shown in Table 8. The viscosity of the hair cosmetic material was measured in the manner described above depending on the value of the viscosity.

[Easiness of Discharge of Hair Cosmetic Material from Container]

The easiness of discharge at the time when the hair cosmetic material was discharged from the agent discharge port 21 was evaluated by clasping the container part 4 with a hand according to the following criteria:
- A: The hair cosmetic material can be easily discharged only by clasping the container part 4 with one hand.
- B: The hair cosmetic material can be discharged by strongly clasping the container part 4 with one hand.
- C: The hair cosmetic material can be discharged by clasping the container part 4 with both hands.

[Easiness of Retention of Hair Cosmetic Material in Application Part]

Easiness of retention of the hair cosmetic material in the application part 2 at the time when the hair cosmetic material was discharged from the agent discharge port 21 by clasping the container part 4 with the hand was evaluated according to the following criteria:
- A: The hair cosmetic material can be filled up to the end part of the comb teeth 22 without dripping the hair cosmetic material from the application part 2.
- B: The hair cosmetic material leaks from the spaces between the comb teeth 22.
- C: Evaluation cannot be done because the hair cosmetic material cannot be contained in the application part 2.

[Easiness of Application of Hair Cosmetic Material]

A wig manufactured by Beaulax Co., Ltd. (an average hair diameter of about 50 μm, and a hair density of 150/cm$^2$) was cut to a hair length of 30 cm. Easiness of application of the hair cosmetic material was evaluated according to the criteria described below, when the container part 4 was clasped with a hand, the hair cosmetic material was discharged from the agent discharge port 21, and it was applied to the wig from the base part to the hair ends.
- A: The hair cosmetic material can be uniformly applied to the wig from the base part to the hair ends (30 cm).
- B: The hair cosmetic material can be uniformly applied to the wig from the base part up to the middle thereof (less than 30 cm).
- C: The hair cosmetic material can be applied to the hair from the base part, but cannot be uniformly applied.
- D: The application is impossible because the hair cosmetic material cannot be contained in the application part.

Examples 1-7 and 1-8, and Comparative Examples 1-1 to 1-3

The percentage of the composition C in the hair cosmetic material was set at the same value as in Example 1-6, and the application of the hair cosmetic material was performed in the same manner as in Example 1-6, except that the ratio of the composition A to the composition B was set at a value shown in Table 8. The same evaluation as in Example 1-6 was performed. The results are shown in Table 8.

Example 1-9

The application of the hair cosmetic material was performed in the same manner as in Example 1-6, except that the ratio of the compositions A, B and C in the hair cosmetic material was changed to value shown in Table 9. The same evaluation as in Example 1-6 was performed. The results are shown in Table 9.

Examples 1-10 to 1-12, and Comparative Example 1-4

Application of a hair cosmetic material was performed in the same manner as in Example 1-6 except that the ratio of the composition A to the composition B in the hair cosmetic material was set at same value as that in Example 1-9, and the percentage of the composition C was set at a value shown in Table 9. The same evaluation as in Example 1-6 was performed. The results are shown in Table 9.

TABLE 5

| | | | Formulation (% by mass) |
|---|---|---|---|
| Composition A | Alkali agent | Aqueous ammonium (28% by mass) | 8.00 |
| | | Ammonium hydrogencarbonate | 1400 |
| | Medium | Water | Balance |
| | Other components | Niacinamide | 3.00 |
| | | Methyl para-oxybenzoate | 0.10 |
| | | Hydroxyethane diphosphonic acid solution (60% by mass) | 1.00 |
| | | Chamomile extract | 0.20 |

TABLE 6

| | | | Formulation (% by mass) |
|---|---|---|---|
| Composition B | Oxidizing agent | Hydrogen peroxide (35% by mass) | 25.72 |
| | Surfactant | Polyoxyethyleneoctyl dodecyl ether | 11.23 |
| | | Polyoxyethylene oleyl ether | 7.83 |
| | | Polyoxyethylene tridecyl ether | 13.05 |
| | | Steary trimethylammonium chloride | 1.70 |
| | pH-controlling agent | Sodium hydroxide | 2.35 |
| | Other components | Isostearyl glyceryl ether | 1.45 |
| | | Isostearylglyceryl pentaerythrityl ether | 3.87 |
| | | Propylene glycol | 11.25 |
| | | Isopropanol | 0.78 |
| | | Ethanol | 10.40 |
| | | Hydroxyethanediphophonic acid | 1.10 |

TABLE 6-continued

| | Formulation (% by mass) | |
|---|---|---|
| | solution (60% by mass) | |
| | 8-Quinolyl sulfate | 0.04 |
| | Perfume | 0.50 |
| | Water | Balance |

TABLE 7

| | | Formulation (% by mass) | |
|---|---|---|---|
| Composition C | Oxidation assistant | Potassium persulfate | 40.20 |
| | | Ammonium persulfate | 18.10 |
| | Alkali agent | Anhydrous sodium meta-silicate | 11.50 |
| | | Sodium carbonate | 0.90 |

TABLE 7-continued

| | Formulation (% by mass) | |
|---|---|---|
| Other components | Sodium carboxymethylcellulose | 7.60 |
| | Xanthan gum | 0.30 |
| | Cornstarch | 2.10 |
| | Hydroxyethyl cellulose | 1.40 |
| | Sylicic anhydride | 2.00 |
| | Diatomaceous earth | 7.18 |
| | Liquid paraffin | 6.20 |
| | Chlorinated O-[2-hydroxy-3-(trimethyl-annmonio)propyl]hydroxyethyl cellulose | 0.10 |
| | Tetrasodium edetate (anhydride) | 2.00 |
| | Ultramarine blue | 0.12 |
| | Perfume | 0.30 |

TABLE 8

| | | Example 1-1 | Example 1-2 | Example 1-3 | Example 1-4 | Comparative Example 1-2 | Comparative Example 1-3 |
|---|---|---|---|---|---|---|---|
| Hair cosmetic material | Weight ratio of mixture (A/B/C) | 52/40/8 | 47/45/8 | 35/57/8 | 57/35/8 | 32/60/8 | 27/65/8 |
| | Viscosity b of hair cosmetic material (Pa·s) | 4.7 | 6.9 | 9.3 | 1.9 | 1.8 | 0.4 |
| | pH of hair cosmetic material | 9.2 | 9.2 | 9.2 | 9.2 | 9.2 | 9.2 |
| Diameter a of liquid-leading passage 51 (mm) | | 7.5 | 7.5 | 7.5 | 7.5 | 7.5 | 7.5 |
| Diameter a of liquid-leading passage (mm)/viscosity b of hair cosmetic material (Pa·s) | | 1.6 | 1.1 | 0.8 | 3.9 | 4.2 | 18.8 |
| Percentage c of head space (%)/viscosity b of hair cosmetic material (Pa·s) | | 7.2 | 4.9 | 3.6 | 17.7 | 18.7 | 84.3 |
| Evaluation | Easiness of discharge of cosmetic material from container | A | A | A | A | A | A |
| | Easiness of retention of cosmetic material in application part | A | A | A | B | B | C |
| | Easiness of application of cosmetic material | B | A | A | C | C | D |

TABLE 9

| | | Example 1-9 | Example 1-10 | Example 1-11 | Example 1-12 | Comparative Example 1-4 |
|---|---|---|---|---|---|---|
| Hair cosmetic material | Mass ratio of mixture (A/B/C) | 36.7/59.7/3.6 | 36.5/59.5/4.0 | 30.4/49.6/20.0 | 28.5/46.5/25.0 | 36.8/59.9/.34 |
| | Viscosity b of hair cosmetic material (Pa·s) | 7.7 | 8.1 | 26.4 | 29.8 | 1.8 |
| | pH of hair cosmetic material | 9.1 | 9.1 | 9.2 | 9.3 | 9.5 |
| Diameter a of liquid-leading passage 51 (mm) | | 7.5 | 7.5 | 7.5 | 7.5 | 7.5 |
| Diameter a of liquid-leading passage (mm)/viscosity b of hair cosmetic material (Pa·s) | | 1.0 | 0.9 | 0.3 | 0.3 | 3.9 |
| Percentage c of head space (%)/viscosity b of hair cosmetic material (Pa·s) | | 4.4 | 4.2 | 1.3 | 1.1 | 17.7 |
| Evaluation | Easiness of discharge of cosmetic material from container | A | A | B | B | A |
| | Easiness of retention of cosmetic material in application part | A | A | A | A | B |
| | Easiness of application of cosmetic material | B | A | A | A | C |

As apparent from the results shown in Table 8 and Table 9, it is found that the hair cosmetic material can be successfully applied in Examples 1-6 to 1-12. On the other hand, it is found in Comparative Examples 1-1 to 1-4 in which the viscosity of the hair cosmetic material is excessively low, the application is unsuccessful.

Example 2-1

Compositions A" and B having formulations shown in Table 10 below were prepared. Each composition was independently contained in a separate container. A container used for containing the composition A" was a bottle having a volume of 37 cm$^3$, and 40 g of the composition A" was contained therein. A container used for containing the composition B was a bottle having a volume of 149 cm$^3$, and 60 g of the composition B was contain therein. The bottle containing the composition B had the same shape and structure as the container part shown by reference sign 4 in FIG. 1, and was a resin bottle having a double nested structure with a squeezable bottomed cylindrical outer container and an inner bag which was disposed in the outer container and whose port was air-tightly joined to an inside surface of a cylindrical port of the outer container.

The bottle containing the composition A" was opened, and the composition A" was added to the bottle containing the composition B. The bottle was closed, and it was shaken in the closed state to promote the mixing. The compositions A" and B were thoroughly mixed as described above to produce a hair cosmetic material. A percentage of a volume of a head space to the volume of the bottle was as shown in Table 1 at that time. The viscosity at 30° C. and the pH at 25° C. of the hair cosmetic material 3 were values shown in Table 1.

Next, the bottle containing the hair cosmetic material 3 was opened, and a member, in which the connection cap 45, the extension part 5 and the application part 2 shown in FIG. 1 were combined, was attached to the opening of the bottle to obtain the applicator 1 shown in FIG. 1. The sizes of the extension part 5, the application part 2 and the container part 4 are as shown in Table 11.

The container part 4 was clasped and squeezed, thereby supplying the hair cosmetic material 3 to application part 2 from the container part 4 through the extension part 5, and the hair cosmetic material was retained in an area surrounded by multiple comb teeth 22 of the application part 2. The application part 2 was put on a base part of hair of a mannequin head, and the application part was moved in the direction of hair ends to apply the hair cosmetic material 3 to the hair. At this time, if the hair cosmetic material 3 could not be applied up to the hair ends because the hair cosmetic material 3 retained in the application part 2 was finished up in the middle of the application, the application was performed while the container part 4 was lightly squeezed during the application to supply the hair cosmetic material 3 to the application part.

The operation described above was performed by 10 panelists, who had rich experience in hair dyeing and bleaching operations, and evaluations of whether or not the hair cosmetic article was acceptable as a product for mass consumption in items of easiness of mixing of the each composition, and easiness of discharge, application and extension, and difficulty of dripping of the hair cosmetic material 3, were performed by them. When 8 or more panelists among the 10 panelists evaluated that it was acceptable, the article was recorded as an acceptable product. The results are shown in Table 11.

TABLE 10

| (% by mass) | | | Example 2-1 |
|---|---|---|---|
| Composition A" | Alkali agent | Strong aqueous ammonia | 8.3 |
| | Dye | Para-aminophenol | 0.2 |
| | | TDA-WM (20% by mass) | 2.5 |
| | | Resorcin | 0.6 |
| | | Meta-aminophenol | 0.1 |
| | Surfactant | Polyoxyethylene (28) cetyl ether | 3.9 |
| | | Stearyl trimethyl-ammonium chloride (28% by mass) | 2.7 |
| | | Dialkyl (12-18) dimethyl ammonium chloride solution (75% by mass) | 0.3 |
| | Oily agent | Stearyl alcohol | 6.3 |
| | | Behenyl alcohol | 1.8 |
| | | Liquid paraffin | 2 |
| | | Oleyl alcohol | 1 |
| | Cationic polymer | Dimethyl diallyl ammonium chloride-acrylamide copolymer solution | 2.5 |
| | | Dimethyl diallyl ammonium chloride-acrylic acid copolymer solution | 3 |
| | Silicones | Mixture of dimethicone and aminoethyl aminopropylmethyl polysiloxane copolymer | 6.8 |
| | Medium | Propylene glycol | 5 |
| | | Purified water | Remaining quantity |
| | Other components | Japanese Pharmacopoeia ascorbic acid | 0.4 |
| | | Anhydrous sodium sulfite | 0.4 |
| | | Tetrasodium edetate dihydrate | 0.1 |
| | | Extract | 0.06 |
| | | Perfume | 0.5 |
| Composition B | Oxidizing agent | Hydrogen peroxide solution (35% by mass) | 15.5 |
| | Surfactant | Polyoxyethylene (15) cethyl ether | 0.39 |
| | | Stearyl trimethyl-ammonium chloride (28% by mass) | 0.5 |
| | Oily agent | Cetyl alcohol | 2 |
| | Medium | Propylene glycol | 0.5 |
| | | Purified water | Remaining quantity |
| | Other components | Oxyquinoline sulfate | 0.04 |
| | | Hydroxyethane diphosphonic acid solution (60% by mass) | 0.07 |
| | | Trimethyl glycine | 1 |
| | | Sodium hydroxide solution (48% by mass) | 0.02 |

TABLE 11

| | | Example 2-1 |
|---|---|---|
| Hair cosmetic material 3 | Weight ratio of mixture (A"/B) | 40/60 |
| | Mass (g) | 100 |
| | Viscosity b of hair cosmetic material (Pa · s) (at 30° C.) | 13 |
| | pH of hair cosmetic material (at 25° C.) | 9.9 |
| Container part 4 | Volume (cm$^3$) | 149 |
| | Minimum cross-section (cm$^2$) | 1.5 |
| | Maximum cross-section (cm$^2$) | 20 |
| | Structure | Outer container/ |

TABLE 11-continued

|  |  | Example 2-1 |
| --- | --- | --- |
|  |  | inner bag |
|  | Percentage c of head space to the volume (%) | 33.7 |
| Agent application part 2 | Height of teeth comb 22 (mm) | 15 |
|  | The number of teeth comb 22 | 15 |
|  | Width of teeth comb 22 (mm) | 2 |
|  | Diameter L4 of circle (mm) | 12 |
| Diameter a of liquid-leading passage 51 (mm) |  | 7.5 |
| Whole length L of applicator 1 (cm) |  | 25 |
| Diameter a of liquid-leading passage (mm)/viscosity b of hair cosmetic material (Pa · s) |  | 0.6 |
| Percentage c of head space (%)/viscosity b of hair cosmetic material (Pa · s) |  | 2.6 |
| Evaluation | Easiness of mixing | Acceptable (10/10) |
|  | Easiness of discharge | Acceptable (10/10) |
|  | Easiness of application | Acceptable (10/10) |
|  | Easiness of extension | Acceptable (10/10) |
|  | Difficulty of dripping | Acceptable (10/10) |

As apparent from the results shown in Table 11, it is found that in the hair cosmetic article in each Example it is easy to mix the each composition. It is also found that it is easy to discharge and apply the hair cosmetic material 3. Furthermore, it is found that it is easy to extend the hair cosmetic material 3 and it is difficult to drip the material in the application operation of the hair cosmetic material 3.

Example 2-2

Compositions A" and B shown in Table 12 below were prepared. Application of a hair cosmetic material was performed in the same manner as in Example 2-1 except that the compositions as above were used. The application operation was performed by 10 panelists, who had rich experience in hair dyeing and bleaching operations, and easiness of discharge of the hair cosmetic material form the container, easiness of retention of the hair cosmetic material in the application part, and easiness of application of the hair cosmetic material were evaluated by them. The evaluation methods are described below. The results are shown in Table 13. The viscosity of the hair cosmetic material was measured in the manner described above depending on the value of the viscosity.

[Easiness of Discharge of Hair Cosmetic Material from Container]

The easiness of discharge at the time when the hair cosmetic material was discharged from the agent discharge port 21 was evaluated by clasping the container part 4 with a hand according to the following criteria:

A: The hair cosmetic material can be easily discharged only by clasping the container part 4 with one hand.

B: The hair cosmetic material can be discharged by strongly clasping the container part 4 with one hand.

C: The hair cosmetic material can be discharged by clasping the container part 4 with both hands.

[Easiness of Retention of Hair Cosmetic Material in Application Part]

Easiness of retention of the hair cosmetic material in the application part 2 at the time when the hair cosmetic material was discharged from the agent discharge port 21 by clasping the container part 4 with the hand was evaluated according to the following criteria:

A: The hair cosmetic material can be filled up to the end part of the comb teeth 22 without dripping the hair cosmetic material from the application part 2.

B: The hair cosmetic material leaks from the spaces between the comb teeth 22.

C: Evaluation cannot be done because the hair cosmetic material cannot be contained in the application part 2.

[Easiness of Application of Hair Cosmetic Material]

A wig manufactured by Beaulax Co., Ltd. (an average hair diameter of about 50 μm, and a hair density of 150/cm$^2$) was cut to a hair length of 30 cm. Easiness of application of the hair cosmetic material was evaluated according to the criteria described below, when the container part 4 was clasped with a hand, the hair cosmetic material was discharged from the agent discharge port 21, and it was applied to the wig from the base part to the hair ends.

A: The hair cosmetic material can be uniformly applied to the wig from the base part to the hair ends (30 cm).

B: The hair cosmetic material can be uniformly applied to the wig from the base part up to the middle thereof (less than 30 cm).

C: The hair cosmetic material can be applied to the hair from the base part, but cannot be uniformly applied.

D: The application is impossible because the hair cosmetic material cannot be contained in the application part.

Examples 2-3 to 2-5 and Comparative Example 2-1

Application of a hair cosmetic material was performed in the same manner as in Example 2-2 except that the ratio of composition A" to the composition B in the hair cosmetic material was set at a value shown in Table 13, and the same evaluation as in Example 2-2 was performed. The results are shown in Table 13.

TABLE 12

|  |  |  | (% by mass) |
| --- | --- | --- | --- |
| Composition A" | Alkali agent | Monoethanolamine | 3.0 |
|  |  | Strong aqueous ammonia (28% by mass) | 8.0 |
|  |  | Ammonium hydrogencarbonate | 1.0 |
|  | Dye | Sulfuric acid toluene-2,5-diamine | 0.9 |
|  |  | Meta-aminophenol | 0.1 |
|  |  | 1-Hydroxyethyl sulfate-4,5-diaminopyrazole | 1.0 |
|  |  | Resorcin | 0.8 |
|  | Surfactant | Stearyl trimethylammonium chloride (28% by mass) | 3.8 |
|  |  | Dialkyl (12-18) dimethyl ammonium chloride solution | 0.3 |
|  |  | Polyoxyethylene cetyl ether | 2.6 |
|  | Oily agent | Behenyl alcohol | 0.3 |
|  |  | Stearyl alcohol | 7.2 |
|  |  | Oleyl alcohol | 1.0 |
|  | Cationic polymer | Dimethyl diallyl ammonium chloride-acrylamide copolymer solution | 2.5 |
|  |  | Dimethyl diallyl ammonium chloride-acrylic acid copolymer solution | 2.5 |
|  | Silicones | Mixture of dimethicone and aminoethyl aminopropyl-methyl polysiloxane copolymer | 3.0 |

TABLE 12-continued

|   |   |   | (% by mass) |
|---|---|---|---|
|   | Medium | Propylene glycol | 5.0 |
|   |   | Purified water | Remaining quantity |
|   | Other components | Tetrasodium edetate dihydrate | 0.1 |
|   |   | Anhydrous sodium sulfite | 0.5 |
|   |   | Ascorbic acid | 0.4 |
|   |   | Extract | 0.03 |
|   |   | Perfume | 0.7 |
| Composition B | Oxidizing agent | Hydrogen peroxide solution (35% by mass) | 16.3 |
|   | Surfactant | Stearyl trimethyl-ammonium chloride (63% by mass) | 1.2 |
|   |   | Dialkyl (12-18) dimethyl ammonium chloride solution | 0.6 |
|   |   | Polyoxyethylene cethyl ether | 0.1 |
|   |   | Polyoxyethylene tridecyl ether | 0.1 |
|   | Oily agent | Oleyl alcohol | 0.5 |
|   |   | Cetyl alcohol | 1.2 |
|   | Medium | Propylene glycol | 1.2 |
|   |   | Purified water | Remaining quantity |
|   | Silicones | Emulsion of aminoethylamino-propylsiloxane-dimethylsiloxane copolymer | 2.0 |
|   | Other components | Oxyquinoline sulfate (2) | 0.04 |
|   |   | Hydroxyethane diphosphonic acid (60% by mass) | 0.07 |
|   |   | Sodium hydroxide solution (48% by mass) | 0.01 |

TABLE 13

|   |   | Example 2-2 | Example 2-3 | Example 2-4 | Example 2-5 | Example 2-1 |
|---|---|---|---|---|---|---|
| Hair cosmetic material | Mass ratio of mixture (A"/B) | 33.4/66.6 | 36/64 | 40/60 | 70/30 | 20/80 |
|   | Viscosity b of hair cosmetic material (Pa·s) (at 30° C.) | 10.7 | 11.4 | 13.0 | 29.7 | 1.9 |
|   | pH of hair cosmetic material (at 25° C.) | 9.7 | 9.8 | 9.8 | 10.0 | 9.6 |
| Percentage c of head space to the volume (%) |   | 33.7 | 33.7 | 10.0 | 33.7 | 33.7 |
| Diameter a of liquid-leading passage 51 (mm) |   | 7.5 | 7.5 | 7.5 | 7.5 | 7.5 |
| Diameter a of liquid-leading passage (mm)/viscosity b of hair cosmetic material (Pa·s) |   | 0.7 | 0.7 | 0.6 | 0.3 | 3.9 |
| Percentage c of head space (%)/viscosity b of hair cosmetic material (Pa·s) |   | 3.1 | 3.0 | 2.6 | 1.1 | 17.7 |
| Evaluation | Easiness of discharge of cosmetic material from container | A | A | A | B | A |
|   | Easiness of retention of cosmetic material in application part | A | A | A | A | B |
|   | Easiness of application of cosmetic material | B | A | A | A | C |

As apparent from the results shown in Table 12 and Table 13, it is found that the hair cosmetic material can be successfully applied in Examples 2-2 to 2-5. On the other hand, it is found that in Comparative Example 2-1 in which the viscosity of the hair cosmetic material is excessively low, the application is unsuccessful.

The invention claimed is:

1. A hair dyeing or bleaching method using a hair cosmetic article, the hair cosmetic article comprising:
   a composition A comprising an alkali agent;
   a composition B comprising an oxidizing agent;
   a composition C comprising a powdery oxidation assistant; and
   a hair cosmetic applicator comprising a container part in which a hair cosmetic material produced by mixing the compositions A, B and C and having a viscosity of 3 to 30 Pa·s at 30° C. is to be contained; an application part by which the hair cosmetic material is applied to a hair-bundle; and an extension part having a liquid-leading passage which communicates the container part to the application part,
   wherein
   the application part includes a discharge port and a comb part, and the comb
   part includes a plurality of comb teeth which are disposed substantially annularly so as to surround the discharge port,
   the method comprising:
   1) mixing the compositions A, B and C in the container part to produce the hair cosmetic material in the container part;
   2) supplying the hair cosmetic material to the application part from the container part through the liquid-leading passage in the extension part using the hair cosmetic applicator, the hair cosmetic applicator being in the state in which the container part in which the hair cosmetic material is contained, the application part, and the extension part are assembled; and 3) applying the hair cosmetic material supplied to the application part to hair.

2. The hair dyeing or bleaching method according to claim 1, wherein the compositions A, B and C are put in the container part, then an opening of the container part is closed with a closing member or the extension part, and the compositions A, B and C are mixed in the closed state.

3. The hair dyeing or bleaching method according to claim 1, wherein a value of a/b is from 0.1 to 5 wherein a denotes a diameter (mm) of the narrowest part of the liquid-leading passage and b denotes a viscosity (Pa·s) of the hair cosmetic material at 30° C.

4. The hair dyeing or bleaching method according to claim 1, wherein a value of c/b is from 0.5 to 15 wherein c denotes a percentage (%) of a volume of a head space to a volume of the container part in the state in which the hair cosmetic material is contained in the container part, and b denotes a viscosity (Pa·s) of the hair cosmetic material at 30° C.

5. The hair dyeing or bleaching method according to claim 1, wherein the hair cosmetic material has a pH of 8 to 12.5 at 25° C.

6. The hair dyeing or bleaching method according to claim 1, wherein the hair cosmetic applicator has a whole length of 5 to 40 cm.

7. The hair dyeing or bleaching method according to claim 1, wherein the comb tooth has a height of 5 to 30 mm.

8. The hair dyeing or bleaching method according to claim 1, wherein a circular line which circumscribes a cross-section of a base end part of each of the comb teeth, and passes a center of the cross-section of the base end part of each of the comb teeth has an internal diameter L4 of from 5 to 30 mm.

9. The hair dyeing or bleaching method according to claim 1, wherein the hair cosmetic material is liquid including a powdery component.

10. A hair dyeing or bleaching method using a hair cosmetic article, the hair cosmetic article comprising:
a composition A' comprising an alkali agent and a powdery oxidation assistant;
a composition B comprising an oxidizing agent; and
a hair cosmetic applicator comprising a container part in which a hair cosmetic material produced by mixing the compositions A' and B and having a viscosity of 3 to 30 Pa·s at 30° C. is to be contained; an application part by which the hair cosmetic material is applied to a hair-bundle; and an extension part having a liquid-leading passage which communicates the container part to the application part,
wherein
the application part comprises a discharge port and a comb part, and the comb part includes a plurality of comb teeth which are disposed substantially annularly so as to surround the discharge port,
the method comprising:
1) mixing the compositions A' and B in the container part to produce the hair cosmetic material in the container part;
2) supplying the hair cosmetic material to the application part from the container part through the liquid-leading passage in the extension part using the hair cosmetic applicator,
the hair cosmetic applicator being in the state in which the container part in which the hair cosmetic material is contained, the application part, and the extension part are assembled; and
3) applying the hair cosmetic material supplied to the application part to hair.

11. The hair dyeing or bleaching method according to claim 10, wherein a value of a/b is from 0.1 to 5 wherein a denotes a diameter (mm) of the narrowest part of the liquid-leading passage and b denotes a viscosity (Pa·s) of the hair cosmetic material at 30° C.

12. The hair dyeing or bleaching method according to claim 10, wherein a value of c/b is from 0.5 to 15 wherein c denotes a percentage (%) of a volume of a head space to a volume of the container part in the state in which the hair cosmetic material is contained in the container part, and b denotes a viscosity (Pa·s) of the hair cosmetic material at 30° C.

13. The hair dyeing or bleaching method according to claim 10, wherein the hair cosmetic material has a pH of 8 to 12.5 at 25° C.

14. The hair dyeing or bleaching method according to claim 10, wherein the hair cosmetic applicator has a whole length of 5 to 40 cm.

15. The hair dyeing or bleaching method according to claim 10, wherein the comb tooth has a height of 5 to 30 mm.

16. The hair dyeing or bleaching method according to claim 10, a circular line which circumscribes a cross-section of a base end part of each of the comb teeth, and passes a center of the cross-section of the base end part of each of the comb teeth has an internal diameter L4 of from 5 to 30 mm.

17. The hair dyeing or bleaching method according to claim 10, wherein the hair cosmetic material is liquid including a powdery component.

18. A hair dyeing or bleaching method using a hair cosmetic article, the hair cosmetic article comprising:
a composition A" comprising an alkali agent and a surfactant;
a composition B comprising an oxidizing agent; and
a hair cosmetic applicator comprising a container part in which a hair cosmetic material produced by mixing the compositions A" and B and having a viscosity of 3 to 30 Pa·s at 30° C. is to be contained; an application part by which the hair cosmetic material is applied to a hair-bundle; and an extension part having a liquid-leading passage which communicates the container part to the application part,
wherein
the application part comprises a discharge port and a comb part, and the comb part includes a plurality of comb teeth which are disposed substantially annularly so as to surround the discharge port,
the method comprising:
1) mixing the compositions A" and B in the container part to produce the hair cosmetic material in the container part;
2) supplying the hair cosmetic material to the application part from the container part through the liquid-leading passage in the extension part using the hair cosmetic applicator,
the hair cosmetic applicator being in the state in which the container part in which the hair cosmetic material is contained, the application part, and the extension part are assembled; and
3) applying the hair cosmetic material supplied to the application part to hair.

19. The hair dyeing or bleaching method according to claim 18, wherein a value of a/b is from 0.1 to 5 wherein a denotes a diameter (mm) of the narrowest part of the liquid-leading passage and b denotes a viscosity (Pa·s) of the hair cosmetic material at 30° C.

20. The hair dyeing or bleaching method according to claim 18, wherein a value of c/b is from 0.5 to 15 wherein c denotes a percentage (%) of a volume of a head space to a volume of the container part in the state in which the hair cosmetic material is contained in the container part, and b denotes a viscosity (Pa·s) of the hair cosmetic material at 30° C.

21. The hair dyeing or bleaching method according to claim 18, wherein the hair cosmetic material has a pH of 8 to 12.5 at 25° C.

22. The hair dyeing or bleaching method according to claim 18, wherein the hair cosmetic applicator has a whole length of 5 to 40 cm.

23. The hair dyeing or bleaching method according to claim 18, wherein the comb tooth has a height of 5 to 30 mm.

24. The hair dyeing or bleaching method according to claim 18, a circular line which circumscribes a cross-section of a base end part of each of the comb teeth, and passes a center of the cross-section of the base end part of each of the comb teeth has an internal diameter L4 of from 5 to 30 mm.

\* \* \* \* \*